US009410939B2

(12) United States Patent
Zernicka-Goetz et al.

(10) Patent No.: US 9,410,939 B2
(45) Date of Patent: Aug. 9, 2016

(54) METHODS FOR PREDICTING MAMMALIAN EMBRYO VIABILITY

(75) Inventors: Magdalena Zernicka-Goetz, Cambridge (GB); Anna Ajduk, Warsaw (PL); Chris Graham, Oxford (GB)

(73) Assignee: Cambridge Enterprise Limited, Cambridge (GB)

( * ) Notice: Subject to any disclaimer, the term of this patent is extended or adjusted under 35 U.S.C. 154(b) by 0 days.

(21) Appl. No.: 14/128,639

(22) PCT Filed: Jun. 29, 2012

(86) PCT No.: PCT/GB2012/051533
§ 371 (c)(1), (2), (4) Date: Mar. 4, 2014

(87) PCT Pub. No.: WO2013/005012
PCT Pub. Date: Jan. 10, 2013

(65) Prior Publication Data

US 2014/0206931 A1 Jul. 24, 2014

Related U.S. Application Data

(60) Provisional application No. 61/577,860, filed on Dec. 20, 2011, provisional application No. 61/503,827, filed on Jul. 1, 2011.

(51) Int. Cl.

| | |
|---|---|
| ***G01N 33/483*** | (2006.01) |
| ***A61D 19/04*** | (2006.01) |
| ***G01N 33/50*** | (2006.01) |
| ***C12M 3/00*** | (2006.01) |
| ***C12M 1/00*** | (2006.01) |
| ***C12M 1/34*** | (2006.01) |

(52) U.S. Cl.
CPC ............ *G01N 33/4833* (2013.01); *A61D 19/04* (2013.01); *C12M 21/06* (2013.01); *C12M 41/14* (2013.01); *C12M 41/26* (2013.01); *C12M 41/46* (2013.01); *G01N 33/5088* (2013.01); *G01N 33/5091* (2013.01)

(58) Field of Classification Search
None
See application file for complete search history.

(56) References Cited

U.S. PATENT DOCUMENTS

2010/0099135 A1 4/2010 Katz-Jaffe et al.

FOREIGN PATENT DOCUMENTS

| | | | |
|---|---|---|---|
| EP | 1847595 | A1 | 10/2007 |
| WO | 2011025736 | A1 | 3/2011 |

OTHER PUBLICATIONS

Ozil, et al. "Ca+2 oscillatory pattern in fertilized mouse eggs affects gene expression and development to term" Developmental Biology, 300: 534-44.*

Nakahara, et al. (2010) "Evaluation of the safety of time-lapse observations for human embryos", Journal of Assisted Reproduction Genetics, 27: 93-96.*

Author unknown, no journal/volume, no pages, http://en.wikipedia.org/w/index.php?title=Special:Book&bookcmd=rendering&return_to=Mammal&collection_id=8979c443305fa5a3651cf7fd6e00d9b50ea66a6b&writer=rdf2latex&is_cached=1, published by Wikipedia, Inc., San Francisco, CA, USA, downloaded as a PDF on May 30, 2015, 15 pages long.*

International Search Report and Written Opinion issued in corresponding International Patent Application No. PCT/GB2012/051533 dated Jan. 11, 2013 (16 pages).

Ajduk et al., "Fertilization Triggers Oscillatory Changes in Velocity of Cytoplasmic Movements in a Mouse Egg," Biology of Reproduction, vol. 81, 2009, Abstract 131, (1 page).

Nakahara et al., "Evaluation of the safety of time-lapse observations for human embryos," Journal of Assisted Reproduction and Genetics, vol. 27, Feb. 2, 2010, pp. 93-96.

Ajduk et al., "Rhythmic actomyosin-driven contractions induced by sperm entry predict mammalian embryo viability," Nature Communications, vol. 2, Aug. 9, 2011, (10 pages).

Adjuk et al., "Advances in embryo selection methods," F1000 Biology Reports, vol. 4, No. 11, Jun. 1, 2012, (5 pages).

* cited by examiner

*Primary Examiner* — Robert M Kelly
(74) *Attorney, Agent, or Firm* — Kilyk & Bowersox, P.L.L.C.

(57) ABSTRACT

The invention provides methods and systems for assessing the developmental potential of mammalian embryos. The method of the invention comprises taking measurements of cytoplasmic movements in the embryo and/or periodic changes in the shape of the embryo at the single cell stage.

24 Claims, 31 Drawing Sheets a Gap43-RFP
UtrCH-GFP
DIC
Gap43/Utrch
b UtrCH-GFP
00:00:13
00:01:33
00:02:53
00:04:13
00:05:33
00:06:53
00:08:13
00:09:33
00:10:53
00:12:13
00:13:33
00:14:53
00:16:13
00:17:33
00:18:53
00:20:13
00:21:33

Green = Tubulin β, Red = actin, Blue = DNA

METHODS FOR PREDICTING MAMMALIAN EMBRYO VIABILITY

This application is a National Stage Application of PCT/GB2012/051533, filed Jun. 29, 2012, which claims priority to U.S. Provisional Patent Application No. 61/577,860, filed Dec. 20, 2011 and U.S. Provisional Patent Application No. 61/503,827, filed Jul. 1, 2011.

FIELD OF INVENTION

The invention provides methods of assessing the developmental potential of a mammalian embryo, methods of selecting or grading embryos from a plurality of embryos according to their predicted developmental potential, and methods of in vitro fertilization (IVF) and assisted reproduction. A system for carrying out the methods of the invention is also provided.

BACKGROUND TO THE INVENTION

There is currently a need for a better means of assessing the vitality of embryos for transplantation into the would-be mother in IVF clinics. The general standard has been to assess the extent of development at 3 days and use this as a predictor of the likely success of subsequent development and hence the pregnancy. The unreliability of this assessment has led an increasing number of IVF clinics to culture embryos until the blastocyst stage (6 days) so that apparently healthy blastocysts can be used directly. Not only is this approach costly but there are inevitable risks from such long term in vitro culture to the blastocyst stage.

The early events in an embryo following fertilization of an egg have been characterized. In mammalian zygotes, sperm entry is linked with reorganization of the cytoskeleton, cortical granules[7], endoplasmic reticulum[8] and mitochondria[9]. Sperm entry causes changes in zygote shape: formation of the second polar body (PB); protrusion of the fertilization cone (FC) above sperm chromatin[17, 18]; and flattening of the zygote along the axis that bisects the FC[19]. Mammalian fertilization also triggers oscillations of free cytoplasmic $Ca^{2+}$ between completion of meiosis and entry into interphase of the first embryonic cell cycle[10]. The $Ca^{2+}$ oscillations regulate not only events immediately following fertilization[11-14], but were also reported to affect aspects of post-implantation development[12, 15, 16]. Both functional actin cytoskeleton and correct pattern of $Ca^{2+}$ transients (especially the total time of $Ca^{2+}$ elevation) have been reported to be crucial for development[12, 15, 16, 37-39].

Cytoplasmic movements triggered by sperm entry have been described in some organisms. In sea urchins, ascidians and frogs, for example, they are known to be associated with successful progress of developmental events, such as the establishment of embryo polarity[1-6]. Some cytoplasmic motions have teen detected in the fertilized mouse egg[20].

Despite this characterization of the events occurring in the embryo immediately after fertilization, assessing the extent of development of the embryos following a period of culture remains the preferred and standard method of assessing embryo quality.

SUMMARY OF THE INVENTION

The present inventors have characterized the cytoplasmic movements triggered by sperm entry into mouse eggs. They have also identified periodic changes in the shape of the embryo that occur following fertilization. They have discovered that the dynamics of these movements can be used to reliably predict the subsequent developmental success of the embryo.

In a first aspect, the invention provides in vitro method of assessing the developmental potential of a mammalian embryo, the method comprising (a) taking measurements of cytoplasmic movements in the embryo and/or periodic changes in the shape of the embryo at the single cell stage, and
(b) using the measurements to predict the developmental potential of the embryo.

An important feature of this method is that it uses measurements taken from the very earliest stages of embryo development after fertilization and before the first embryonic cell division. The method thus provides an advantageously early and fast way of assessing an embryo's quality and likely subsequent developmental success.

The inventors have identified a significant correlation between parameters relating to the average speed of the cytoplasmic movements in mouse embryos at the single cell stage and indicators of subsequent developmental success.

Distinct periodic peaks in the average speed of cytoplasmic movement, referred to herein as "speed peaks", have been observed by the inventors in mouse embryos following fertilization. They have found that the length of the interval between speed peaks is predictive of the developmental success of the embryo. Longer intervals between speed peaks correlates with greater developmental success.

In some cases in accordance with the method of the invention, the developmental potential of an embryo is predicted by measuring the mean cytoplasmic speed in the embryo at the single cell stage over a period of time that is sufficient to identify two successive speed peaks and calculating the interval in time between the two speed peaks. A longer interval or a longer average interval between speed peaks may correlate with a prediction of greater developmental potential. In some cases, a shorter interval or a shorter average interval between speed peaks may correlate with a prediction of greater developmental potential. In some cases, the developmental potential of the embryo is predicted by comparing the interval or the average interval between speed peaks with one or more pre-determined reference values.

When the fertilization cone of the embryo is formed, the speed peaks coincide with periodic changes in the shape of the embryo. Most strikingly, the speed peaks coincide with pulsations of the fertilization cone (FC pulsations). The periodic changes in the shape of the embryo such as the FC pulsations can also therefore be predictive of developmental potential.

A second parameter that significantly correlates with developmental success is the average basal cytoplasmic speed. This is the average speed before the first speed peak recorded, in between speed peaks and/or after the last recorded speed peak. The inventors have found that the average basal cytoplasmic speed is predictive of the developmental success of the embryo. A faster average basal cytoplasmic speed correlates with greater developmental success.

In some cases in accordance with the method of the invention, the developmental potential of an embryo is predicted by measuring the average basal cytoplasmic speed in the embryo before the first speed peak recorded, in between speed peaks and/or after the last distinct speed peak recorded. A faster average basal cytoplasmic speed may correlate with a prediction of greater developmental potential. In some cases, a slower average basal cytoplasmic speed may correlate with greater developmental potential. In some cases, the developmental potential of the embryo is predicted by comparing the average basal cytoplasmic speed with one or more pre-determined reference values.

The prediction of developmental potential may be improved by using both of these parameters together. In some cases in accordance with the method of the invention, the prediction of developmental potential is based on both the length of the interval between speed peaks or FC pulsations and the average basal cytoplasmic speed. These parameters may have been calculated using measurements of the embryos taken over the same period of time. In general, the inventors have found that embryos predicted to have high or low developmental potential based on the length of their inter-peak intervals are correspondingly also predicted to have high or low developmental potential based on their average basal cytoplasmic speed. That is, the predictions based on these two parameters tend to correspond.

The method of the invention offers a fast way to predict the vitality of eggs fertilized in vitro at an early stage after fertilization, i.e. before the first embryonic cell division, and could therefore improve the prospects for in vitro fertilization (IVF) treatment.

In a further aspect the invention provides a method of in vitro fertilization, comprising fertilizing a mammalian egg and predicting the developmental potential of the resulting embryo using measurements of cytoplasmic movements in the embryo and/or periodic changes in the shape of the embryo at the single cell stage. In vitro fertilized eggs predicted to have good developmental potential may, for example, be selected for transfer to a maternal recipient, thereby improving successful pregnancy rates.

Also provided is a method of assisted reproduction, the method comprising predicting the development potential of a mammalian embryo using measurements of cytoplasmic movements in the embryo and/or periodic changes in the shape of the embryo at the single cell stage, and subsequently transferring the embryo to a maternal recipient.

In some cases the absolute quality of a given embryo is of less importance than the relative quality of the embryos in a group of embryos, for example the embryos developed from eggs obtained from the same mother.

A further aspect of the invention provides a method of selecting one or more embryos from a plurality of embryos, the method comprising predicting the developmental potential of each embryo using measurements of cytoplasmic movements in the embryo and/or periodic changes in the shape of the embryo at the single cell stage, and selecting one or more embryos based on their predicted developmental potential. Other factors may also be taken into account when selecting the embryo(s). The one or more embryos may be selected for use in a method of assisted reproduction.

Another aspect of the invention provides a method of grading a one or more embryos in a population of embryos according to their developmental potential, the method comprising predicting the developmental potential of each embryo using measurements of cytoplasmic movements in the embryo and/or periodic changes in the shape of the embryo at the single cell stage, and grading each embryo based on its predicted developmental potential. One or more embryos may further be selected based on their predicted developmental potential. The one or more embryos may be selected for use in a method of assisted reproduction.

In a further aspect, the invention provides a system for carrying out the method of the invention, the system comprising one or more sensors for capturing time lapse images of the embryos and at least one processor in communication with the at least one sensor, the processor being programmed with computer-readable instructions to transform said images into a prediction of the developmental potential of the embryo.

The invention will now be described in more detail, by way of example and not limitation, by reference to the accompanying drawings. Many equivalent modifications and variations will be apparent to those skilled in the art when given this disclosure. Accordingly, the exemplary embodiments of the invention set forth are considered to be illustrative and not limiting. Various changes to the described embodiments may be made without departing from the scope of the invention. All documents cited herein are expressly incorporated by reference.

The present invention includes the combination of the aspects and preferred features described except where such a combination is clearly impermissible or is stated to be expressly avoided.

Section headings are used herein are for convenience only and are not to be construed as limiting in any way.

References to color in the figures are for information only. There are no color figures.

Figure 1A:
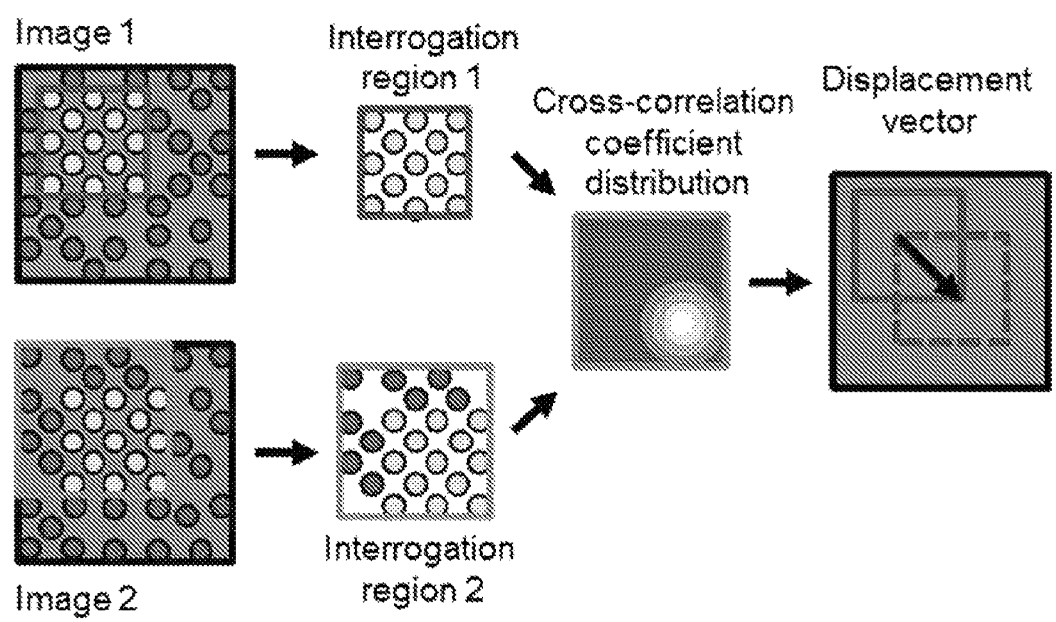
FIG. 1

Oscillations of Cytoplasmic Speed in Fertilized Mouse Eggs (a) Schematic of the cross-correlation image analysis algorithm used to measure the movement of the cell cytoplasm (detailed description in Methods). (b) A schematic representation of the analyzed stages: MII: unfertilized eggs in metaphase of the $2^{nd}$ meiotic division. Stage 1: 2PB is formed and FC first appears. Stage 2: FC is fully formed. Stage 3: FC regresses and pronuclei are formed. (c) Mean cytoplasmic speed in a representative unfertilized egg. (d) Mean cytoplasmic speed in a representative in vivo fertilized zygote during Stages 1 to 3. (e) DIC images with vector patterns representative for unfertilized eggs (MII) and for zygotes in Stage 1 to 3. For clarity only every second vector is shown. Length of the vectors and color of the background indicate speed of the local cytoplasmic movement. Scale bar 10 μm.

FIG. 2

Cytoplasmic Speed-Peaks Depend on Changes in the Actomyosin Cytoskeleton in the FC Region (a) DIC images of the zygote with a pulsating FC: the FC (marked with an asterisk) protrudes and flattens in a repetitive way. Scale bar 20 μm (b) Peaks of the mean cytoplasmic speed in the fertilized mouse egg (blue/bottom line) correlate with the beginning of a decrease in the FC diameter (green/top line). The FC diameter was measured as shown in (a) from the point of maximum symmetry on the edge of the FC to the other edge of the cell. (c) Change in the FC diameter (measured as a difference between FC diameter immediately before the speed-peak and at the timepoint when the speed-peak reaches its maximum) correlates with the amplitude of the accompanying speed-peak. The Pearson correlation coefficient calculated for these measurements is 0.595 and is statistically significant ($p<0.0001$). (d) Intensity of UtrCH-EGFP fluorescence in the cortex of the FC (blue/bottom line) fluctuates as the FC changes its shape (as shown by changes in the FC diameter (red/top line)). Intensity values are presented as a ratio between UtrCH-EGFP and Gap43-RFP (a membrane protein) fluorescence, to eliminate intensity changes caused by shifts in the focus (see Methods for the details). Asterisks show ends of the cortical region in which intensities of UtrCH-EGFP and Gap43-RFP were measured. Scale bar 10 μm. (e) Intensity of MyoRLC-GFP fluorescence in the lower and upper shoulder of the FC (blue line and blue line with crosses, respectively) fluctuates as the FC changes its shape (as shown by changes in the FC diameter (red)). Intensity values are presented as a ratio between UtrCH-EGFP and Gap43-RFP fluorescence. Asterisks mark the regions in which intensities of MyoRLC-GFP and Gap43-RFP were measured. Scale bar 10 μm. (f) Mean cytoplasmic speed in representative zygotes treated with nocodazole (blue (top) line), cytochalasin D (red (bottom) line) and ML-7 (green (middle) line). (g) Mean cytoplasmic speed in representative zygotes treated with taxol (blue (top) line) and jasplakinolide (red (bottom) line). The peak visible at approx. 90 min is due to a shift in focus.

FIG. 3

Cytoplasmic Speed Peaks Depend on Free $Ca^{2+}$ Oscillations

Peaks of mean cytoplasmic speed (blue/bottom lines) and free $Ca^{2+}$ levels (green/top lines) in a representative fertilized egg (a), fertilized egg treated with BAPTA-AM (b) and egg activated with $SrCl_2$ (c). When eggs were activated with $SrCl_2$, $Ca^{2+}$ transients were not accompanied by even small speed-peaks (insert in (c)). In all graphs the increase in $Ca^{2+}$ level was reflected by a decrease in the intensity of FuraRed fluorescence. A peak in (b) was due to a shift in focus.

FIG. 4

High Amplitude Cytoplasmic Speed-Peaks Depend on the Presence of the FC

Mean cytoplasmic speed (blue/bottom lines) and free $Ca^{2+}$ levels (green/top lines) in representative eggs subjected to intracytoplasmic sperm injection (ICSI). A fresh sperm head was injected under the cortex (a) or in the central part of the cytoplasm (b). A heat-inactivated sperm head was injected under the cortex and then the egg was either activated (c) or not activated (d) with $SrCl_2$. In eggs injected with heated sperm heads and activated with $SrCl_2$ small speed-peaks were frequently present (insert in (c)). In all graphs the increase in $Ca^{2+}$ level was reflected by a decrease in the intensity of FuraRed fluorescence.

FIG. 5

Cytoplasmic Movements as an Indicator for Viability of Embryos

Correlation between mean basal speeds (a) or mean inter-speed-peak intervals (b) recorded in zygotes and the number of cells in the embryos after 4 days of culture. (c) Mathematical model fitted to the data in (a), showing linear and quadratic correlation between mean basal speeds and number of cells in the 4-day-old embryos with an adjustment for different values of the mean inter-peak intervals. Mean inter-peak interval+1 SD (top line), mean inter-peak interval+0.5 SD (second line down), mean inter-peak interval (third line down), mean inter-peak interval−0.5 SD (fourth line down), mean inter-peak interval−1 SD (bottom line). (d) Mathematical model fitted to the data in (b), showing linear correlation between mean inter-peak intervals and number of cells in the 4-day-old embryos with an adjustment for different values of the mean basal speeds. Mean inter-peak interval+1 SD (top line), mean inter-peak interval+0.5 SD (second line down), mean inter-peak interval (third line down), mean inter-peak interval−0.5 SD (fourth line down), mean inter-peak interval−1 SD (bottom line). Graphic representation of the models in (c) and (d) was prepared for values in range indicated with red brackets in (a) and (b), respectively. (e) An egg cylinder (left) and 2-week old pups (right) obtained from embryos scored as 'good' based on our model. Actin labeled with phalloidin in green and Gata4 marking visceral endoderm in red. Scale bar 50 μm. (f) Efficiency of embryo transfers. Embryos were scored as of 'high' or 'low quality' according to our model, transferred at 2-cell stage to the recipient females and dissected at 6.5 (blue (solid) columns) or 19.5 dpc (red (hatched) columns).

FIG. 6

PLCζ- and ICSI-induced $Ca^{2+}$ oscillations in human oocytes are accompanied by co-incident transient movements in the oocyte cytoplasm. In A) is shown a recording of intracellular $Ca^{2+}$ increases as measured by fluorescence of Oregon Green BAPTA dextran (OGBD) (arbitrary units) and the corresponding movements in the cytoplasm as measured with PIV. The traces in B) show the initial phases of $Ca^{2+}$ and PIV, respectively, from another oocyte that showed a large initial $Ca^{2+}$ increase with a decrease in movement. Spikes marked with * are shown at an expanded scale in FIG. 7.

FIG. 7

Coincidence analysis of $Ca^{2+}$ changes and cytoplasmic movement. These panels with an expanded time scale are taken from the oocyte in FIG. 6B. The first $Ca^{2+}$ spike lasts for a long period and cytoplasmic movement is suppressed. Later $Ca^{2+}$ spikes are shorter and the mean magnitude of movement in the speed-peak increases to a maximum shortly after the spike maximum. In the illustrated case, the speed-peak maximum occurs 20 sec after the $Ca^{2+}$ maximum. Note that the mean magnitude of movement starts to accelerate within the same 10 sec interval as the $Ca^{2+}$ maximum.

FIG. 8

Images of a human oocyte overlaid with the pattern of cytoplasmic movement. Each vector map records movement during the 10 sec interval between one frame and the next. This pair of vector maps was collected 20 secs apart and they illustrate the reversal of movement direction without alteration in movement orientation.

FIG. 9

Cytoplasmic Movements in the Zygote

Mean cytoplasmic speed in a zygote imaged in a plane above the FC (a), a plane bisecting the FC (c) and a plane below the FC (e). (b), (d) and (f) Cytoplasmic speeds in a timepoints marked by an arrow in (a), (c) and (e) respectively. Colour of the background represents local speed values. FC visible at 5 o'clock. Scale bar 10 μm. (g) Speed-peaks recorded during the first and second $Ca^{2+}$ transients in the egg injected with sperm.

FIG. 10

Reorganization of Actin in the Cortex of the Fertilization Cone.

(a) Still images from a time-lapse movie showing reorganization of actin (labeled with UtrCH-EGFP) in the FC. UtrCH-EGFP intensity in the FC cortex changes in accordance to the change in the FC shape. As the FC flattens (beginning of the flattening marked with a red line) intensity of UtrCH-EGFP, labeling F-actin, weakens. When the FC starts gradually protruding, intensity of UtrCH-EGFP increases again. Gap43-RFP served as a membrane marker. Images were taken every 20 s, every $4^{th}$ image is shown. (b) Zoomed images of the FC cortical region indicated in (a). Scale bar 10 μm.

FIG. 11

Reorganization of Myosin in the Cortex of the Fertilization Cone.

(a) Still images from a time-lapse movie showing reorganization of myosin (labeled with MyoRLC-GFP) in the FC. MyoRLC-GFP intensity in the cortex of the FC shoulders changes in accordance to the change in the FC shape. As the FC flattens (beginning of the flattening marked with a red line) intensity of MyoRLC-GFP weakens. When the FC starts gradually protruding, intensity of MyoRLC-GFP increases again. Gap43-RFP served as a membrane marker. Images were taken every 20 s, every $2^{nd}$ image is shown. (b) and (c) Zoomed images of the FC cortical region indicated in (a) by numbers 1 and 2 respectively.

Scale bar 10 μm.

FIG. 12

Effect of $Ca^{2+}$ Chelatation and Cytoskeletal Inhibitors on Microtubules and Actomyosin in Mouse Zygotes.

Fertilized in vitro eggs were transferred to the inhibitors when anaphase bulges appeared. Images show projections prepared from confocal Z-stacks of representative zygotes fixed immediately after 20 minutes of preincubation with the drug (20+0 min) or 1.5 or 3 hours later (0+90 min and 0+180 min, respectively). Experimental and contro zygotes were scanned using the same settings. Phalloidin staining of jasplakinolide-treated zygotes failed to show F-actin (third panel from the bottom), because jasplakinolide competes with phalloidin for the same binding sites and thus prevents proper staining. Staining with anti-actin antibody revealed that jasplakinolide leads to formation of a thicker cortical layer of actin (2 bottom panels). Female chromatin indicated by f, male chromatin indicated by m. Scale bar 10 μm.

FIG. 13

DIC Imaging does not Affect Development of the Mouse Embryos.

(a) Mathematical model correlating probability of achieving blastocyt stage with mean basal speed with an adjustment for mean inter-peak intervals. Mean inter-peak interval+1 SD (top line), mean inter-peak interval+0.5 SD (second line down), mean inter-peak interval (third line down), mean inter-peak interval−0.5 SD (fourth line down), mean inter-peak interval−1 SD (bottom line). (b) Mathematical model correlating probability of achieving blastocyt stage (i.e≥32 cells) with mean inter-peak interval with an adjustment for mean basal speed. Mean inter-peak interval+1 SD (top line), mean inter-peak interval+0.5 SD (second line down), mean inter-peak interval (third line down), mean inter-peak interval−0.5 SD (fourth line down), mean inter-peak interval−1 SD (bottom line). (c) Mean number of cells in 4-day-old embryos imaged at different times after fertilisation. (d) Distribution of 4-day-old embryos with different number of cells in relation to the time of pronuclear formation. (e) Mean number of cells in 4-day-old embryos imaged or not in the zygote stage. (f) Distribution of 4-day-old embryos with different number of cells depending on whether they were or were not imaged in the zygote stage. Error bars represent standard deviations. Data comes from 13 independent experiments.

FIG. 14

Subpixel Resolution of the PIV Method

Accuracy of PIV for measuring sub-pixel displacements of artificially shifted and down sampled images. (a) Error in pixels. (a) Error as a percentage of the displacement.

DETAILED DESCRIPTION OF THE INVENTION

The term "embryo" is used in this specification to refer to a mammalian organism from the earliest stage starting with a single cell fertilized egg. An egg is fertilized on fusion with a sperm. The egg may have been fertilized in vitro to obtain the embryo. The single cell embryos are living cells.

The methods of the invention may be applied to embryos from any suitable mammalian species, such as: primates, including humans, great apes (e.g. gorillas, chimpanzees, orang utans), old world monkeys, new world monkeys; rodents (e.g. mice, rats, guinea pigs, hamsters); cats; dogs; lagomorphs (including rabbits); cows; sheep; goats; horses; pigs; and any other livestock, agricultural, laboratory or domestic mammals. Although the work described in the Examples was carried out in mice, preliminary results indicate that a similar pattern of cytoplasmic movements also occurs in human single cell embryos.

The "developmental potential" of a mammalian embryo is a measure of the quality of the embryo. It is a measure of the ability of the embryo to subsequently develop successfully. Successful development may be over a defined period of time or under particular conditions, for example following growth in culture or following transfer of the embryo to a maternal recipient. Transfer to a maternal recipient means the transfer of an embryo into a would-be mother with the aim of a resulting pregnancy. The mother may be the donor or source of the eggs (female gametes) that gave rise the embryo or may be a surrogate mother.

A prediction of the developmental potential of an embryo is a prediction of the ability of the embryo to subsequently develop successfully. A prediction of developmental potential may comprise a prediction of whether the embryo has the ability to develop to a particular stage. Examples are a prediction that an embryo will reach the blastocyst stage if grown in culture, or that an embryo will develop to the egg cylinder stage or to full term following transfer of the embryo to a maternal recipient. The prediction may comprise a determined probability that the embryo will reach a particular stage of development, or the probability that a particular stage of development will be reached within a defined period of time. For example, the prediction may define the probability that an embryo will reach the blastocyst stage after 4 days of growth in culture. It is not necessary that the embryo is subsequently cultured in accordance with the prediction. The embryo may instead be transferred to a maternal recipient. The prediction may comprise a prediction of the stage of development that the embryo will reach after a defined period of time. An example is a prediction of the number of cells that an embryo will have after a period of time in culture, for example following 1, 2, 3, 4, 5, 6 or more days of growth in culture.

In some cases the prediction of developmental potential is based on measurements of the cytoplasmic movements in the embryo and/or periodic changes in the shape of the embryo alone. In other embodiments the prediction of developmental prediction is based on these measurements in conjunction with other parameters that are known to be predictive of developmental success. For example, after taking measurements of the cytoplasmic movements and/or periodic changes in the shape of the embryo in the single cell embryo, the embryo may subsequently be cultured and the extent of development and/or morphology of the embryo in culture further used in assessing the developmental potential of the embryo.

The term "cytoplasmic movement" refers to the fluid dynamics of the cytoplasm. The cytoplasm is the fluid phase in a single cell embryo. There is no conventional nucleus in an unfertilized or fertilized egg until the haploid chromosome complement of the second division of female meiosis decondenses and acquires a nuclear envelope and, for fertilised eggs, until the sperm chromatin becomes correctly associated with histones and encapsulated with a nuclear envelope. Such formation of the female and male pronuclei precede the first embryonic cell division. The cytoplasmic movements as described herein occur until the time of pronuclei formation.

The term "average" as used in this specification refers to a measure of central tendency. "Average" encompasses the mean and the median.

The "average cytoplasmic speed" means the average speed at any particular time as measured in a single plane through the single cell embryo or in the cytoplasm as a whole, for example as measured in a series of planes through the whole cell.

The inventors have shown that before fertilization, the cytoplasmic movement in a mouse egg is slow and relatively homogenous. Fertilization triggers dramatic periodic increases and decreases in the velocity of the cytoplasmic movements in the egg. These abrupt, periodic and transient cytoplasmic flows are distinct from the lower speed movements that occur in between and are herein referred to as "speed-peaks".

The term "after-movements" refers to cytoplasmic movements that may occur immediately after the dramatic decrease in speed of a speed peak, but that that are of greater amplitude than and can be distinguished from the slower movements that occur in between speed peaks. A speed peak may include the after-movements.

The speed peaks occur throughout the egg cytoplasm and may last for approximately 4 hours after fertilization, until pronuclei formation. The speed peaks can be identified by measuring the mean cytoplasmic speed in an embryo over time during this period. The speed peaks can be identified in any plane through the single cell embryo. However the amplitude of the speed peaks is greatest in the equatorial plane of the cell.

The amplitude of the speed peaks may vary over time. The first speed peak may be of relatively high amplitude, followed by a period in which the speed peaks have relatively low amplitude (between the onset of anaphase of meiosis II and early FC outgrowth, herein referred to as "stage 1"). When the FC is fully formed or extended (herein referred to as "stage 2"), the amplitudes of the speed peaks may be greater. The amplitude of the speed peaks may decrease during and following FC regression (herein referred to as "stage 3").

The direction or vector of the rapid cytoplasmic movement of a speed peak may vary between speed peaks recorded from the same fertilized egg. During stage 1, the vectors are typically towards the developing second polar body (PB). During stage 2, the vectors are typically directly towards the FC or slightly displaced towards the second polar body.

If two successive speed peaks in the cytoplasmic movement in a single cell embryo are identified, then the interval in time between them can be measured. If more than two successive speed peaks are identified, then the average interval between speed peaks in the embryo can be determined.

The fertilization cone (FC) is a transient conical projection that protrudes from the surface of a fertilized egg at the point of contact with the fertilizing sperm.

The speed peaks or FC pulsations may also be synchronous with $Ca^{2+}$ transients in the embryo.

The "average basal cytoplasmic speed" is the average cytoplasmic speed over time during the period before the first speed peak that is recorded, during the period in between speed peaks and/or during the period after the last speed peak that is recorded. The average basal cytoplasmic speed may be measured at any time during one or more of these periods. In some cases in accordance with the method of the invention, the mean cytoplasmic speed is measured up to the first speed peak that is recorded, from immediately after one distinct speed peak to the beginning of the next distinct speed peak, and/or immediately after the last distinct speed peak that is recorded. The average basal cytoplasmic speed may be determined over these periods.

In some cases the developmental potential of an embryo is predicted by comparing the interval between speed peaks or FC pulsations, the average interval between speed peaks or FC pulsations, or the average basal cytoplasmic speed, with one or more pre-determined reference values. The reference values may have been determined empirically based on previous data correlating these parameters to indicators of high or low developmental potential.

In some cases the measurements are taken when the embryo is at a stage of development between fertilization and formation of the pronuclei. The "formation of the pronuclei" is the decondensing of the sperm and egg chromatin and formation of the interphase nucleus containing the smaller nucleoli. The skilled person can identify this in bright fields or DIC (differential interference contrast) images.

In some cases the single cell embryo is at a stage of development between fertilization and regression of the fertilization cone. In some cases the single cell embryo is at a stage of development after extrusion of the polar body and before formation of the pronuclei, or before regression of the fertilization cone. Extrusion of the polar body is when the edges of the polar body in the contact zone with the egg rounded up suggesting that the cleavage furrow tightens up.

In some cases the embryo is in a stage of development wherein the fertilization cone is fully formed. This is the period between formation and regression of the fertilization cone In some cases the prediction of developmental potential is based on measurements of the cytoplasmic movements taken throughout the period when the fertilization cone is present. In mice, the fertilization cone is present for approximately 2 hours, starting from approximately 1-1.5 hrs after fertilization. Typically the fertilization cone will start to form about two hours after incubation with sperm when the egg is fertilized in vitro. In some cases in accordance with the method of the invention the measurements are taken after two hours of co-incubation of sperm with an egg.

In some cases, taking the measurements comprises time lapse image capture followed by quantitative image analysis.

The time lapse images may be captured from a single plane through the single cell embryo. The speed peaks are fastest and therefore most easily distinguished during stage 2 when the FC is fully formed and the cytoplasmic movement of the speed peaks is typically directed towards the FC. The speed peaks are also fastest in the equatorial plane of the cell. The equatorial plane is also the biggest and gives the best quality image. Preferably the time lapse images are captured from a single plane through the centre of the cell. Preferably the time lapse images are captured from a single plane that bisects the FC equatorially.

The embryos that are assessed according to the method of the invention may be intended for use in subsequent downstream procedures, such as experimental uses or transfer to a maternal recipient resulting in pregnancy. It is therefore important to minimise any damage to the embryos whilst carrying out the method of assessment. The method of the invention may be a non-invasive. For example, one of the advantages of the method of the invention is that it can be carried out in the absence of any dye, for example fluorescent dye, added to the cell.

Furthermore, the inventors have found that the speed peaks, which coincide with pulsations of the fertilization cone, are dependent on the dynamics of the actomyosin cytoskeleton. Therefore, to minimise potential effects on the innate pattern of cytoplasmic movements and changes of shape of the embryo, the measurements are preferably taken in a way that does not interfere with or minimises interference with the function or dynamics of the cytoskeleton and/or formation of the fertilization cone.

In a particularly preferred embodiment, the single cell embryo that is imaged is held in a tight group of single cell embryos in a small drop of medium. Preferably the small drop of medium is less than 30 μl, or less than 20 μl in volume. The volume may be 5-10 μl in volume. The inventors have found that this is an effective way of stabilizing the position of the embryos, that is holding the embryos still, without affecting the structural dynamics of the cell.

Alternatively, the embryo may be a single embryo in the drop of medium.

The medium may be buffered, for example with HEPES, to keep a constant pH. Alternatively an environmental chamber can be used to maintain a steady pH. The environmental chamber may provide $CO_2$, for example 5% $CO_2$ to keep the pH of the medium at the correct level.

An environmental chamber may also be used to regulate the temperature of the embryos during imaging. For example the temperature may be maintained at 35 to 40° C., or 37 to 38° C. or at about 37.5° C. The temperature may also be controlled by using a heated stage.

Preferably the images are captured using light that does not damage the embryos. For example, long exposure, intense light or short wavelengths might damage DNA and the respiratory chain through production of reactive oxygen species. The irradiance and exposure time might be minimised by selection of, for example, rapid lamp shutter speeds or light emitting diode (LED) light sources, and by use of very sensitive sensors to collect images. Appropriate wavelengths might be selected by the use of optical filters or single wavelength LED light sources. White transmitted light may be used.

Imaging systems suitable for measuring cytoplasmic movements and changes in cell shape might use bright field microscopy. Alternatively they might use high contrast techniques that include, for example, differential interference contrast (DIC), Hoffman modulation contrast or phase contrast microscopy.

Another advantage of the present invention is that it provides a way of assessing the developmental potential of an embryo very early on, from measurements taken over a short period of time from embryos in the very earliest stage of development before the first embryonic cell division. In some cases, the relevant measurements are all taken within 6 hours, more preferably within 5, 4, 3, 2 or 1 hour of fertilization. In some cases the measurements are all taken before pronuclei formation in the embryo. More preferably the measurements are all taken before regression of the FC. For example the time lapse images of the embryo may all be captured within these periods of time. In some cases the method is completed, including the prediction of developmental potential, within 6 days, more preferably within 4, 3, 2 or 1 day of fertilization, or within 12, 6, 4, 3, 2 or 1 hours of fertilization.

In some cases the quantitative image analysis uses particle image velocimetry (PIV). PIV is a standard analysis technique used extensively in fluid dynamics[21-24] that involves cross-correlating image sub-regions between sequential pairs of images. Using PIV analysis each image can be divided into square interrogation regions and the cross-correlation coefficient distribution can be calculated within a larger region in the next image in the sequence. The peak of the cross-correlation coefficient distribution gives the most likely location in the second image of the material in the interrogation region in the first image. This can then be used to calculate the displacement vector over the time between images (FIG. 1A). As the displacement of the pattern of contrast of an area of pixels is measured over many pixels it is possible to accurately measure sub-pixel movements with this technique[22, 24, 48]

In some cases in accordance with the invention, one or more embryos in a population of embryos can be graded according to their developmental potential. The developmental potential of each embryo can be graded relative to the developmental potential of the other embryos in the population. This may provide a useful way of determining which embryos from the population of embryos are most suitable for a particular subsequent intended use, for example transfer to a maternal recipient with the aim of a resulting pregnancy. Embryos can thereby be selected according to their developmental potential.

The method may involve calculating the population mean interval or average interval between speed peaks or FC pulsations, and/or the population mean average basal cytoplasmic speed. The method may involve calculating the population standard deviations for these parameters. Obvious outliers in the population may be excluded from the calculations. For example, embryos that have a calculated interval or average interval between speed peaks or FC pulsations or a calculated average basal cytoplasmic speed that is more than 1 standard deviation, or more than 1.5 standard deviations, or more than 2 standard deviations, or more than 3 standard deviations away from the mean, or that are in the top and/or bottom 10% of calculated values may be excluded. The population mean and/or standard deviations can be used to quantify the relative developmental potential of one or more of the embryos in the population. For example having a calculated interval or average interval between speed peaks that is longer than the population mean interval or average interval between speed peaks, and/or having an average basal cytoplasmic speed that is faster than the population mean average basal cytoplasmic speed may be indicative of an embryo having high developmental potential.

Conversely having a calculated interval or average interval between speed peaks that is shorter than the population mean interval or average interval between speed peaks, and/or having an average basal cytoplasmic speed that is slower than the population mean average basal cytoplasmic speed, may be indicative of an embryo having high developmental potential. Similarly having a calculated interval or average interval between speed peaks that is at least half, or at least a third or at least a quarter or at least one, two or three standard deviations longer or shorter than the population mean interval or average interval between speed peaks, and/or having an average basal cytoplasmic speed that is at least half, or at least a third, or at least a quarter, or at least one, two or three standard deviation faster or slower than the population mean average basal cytoplasmic speed of the population may be indicative of an embryo having high or low developmental potential respectively.

EXAMPLES

Combining a rapid imaging of the freshly fertilized mouse egg with advanced image analysis based on particle image velocimetry reveals that fertilization induces rhythmical cytoplasmic movements that coincide with pulsations of the protrusion forming above the sperm head. We found that these movements are caused by contractions of the actomyosin cytoskeleton triggered by $Ca^{2+}$ oscillations induced by fertilization. Most importantly, the relationship between the movements and the events of egg activation makes it possible to use the movements alone to predict whether a zygote will develop successfully. This method offers thus far the earliest and fastest, non-invasive way to predict the vitality of eggs fertilized in vitro and therefore can potentially improve greatly the prospects for IVF treatment.

Methods

Collection of Eggs and Sperm

F1 (C57B16×CBA) mouse females were superovulated and oocytes and zygotes recovered as described previously[44]. Parthenogenetic activation was performed by incubating eggs for 4 hrs in M2 medium without $Ca^{2+}/Mg^{2+}$ supplemented with 10 mM $SrCl_2$. Germinal vesicle (GV) oocytes were isolated from ovaries to M2 medium supplemented with 150 μg/ml dibutyryl cyclic AMP (dbcAMP). Epididymal sperm was isolated from F1 males and capacitated in 0.5 ml of fertilization medium with 4 mg/ml BSA[45]. Embryos were imaged in KSOM medium as described previously[44]. In some experiments prior to imaging embryos were pre-incubated for 20 min with 30 μM BAPTA-AM (to chelate $Ca^{2+}$), 5 μg/ml nocodazole (to depolimerize microtubules), 2 μg/ml cytochalasin D (to depolimerize F-actin), 10 μM taxol (to stabilize microtubules) or 100 nM jasplakinolide (to stabilize F-actin) and then transferred to pure KSOM (BAPTA-treated embryos) or to KSOM containing the respective drug (rest of the treated embryos). Embryos treated with ML-7 (to inhibit myosin light chain kinase (MLCK) and therefore myosin II activation[46]) were pre-incubated with 25 μM ML-7 for 20 mins and then imaged in a dish containing KSOM with 25 μM ML-7 without a mineral oil overlay which would have absorbed ML-7.

Imaging and Cross-Correlation Analysis of Cytoplasmic Movements

In most experiments zygotes were imaged in a single plane under an inverted confocal microscope (Zeiss LSM 510 Meta) at 37.5° C. and 5% $CO_2$. DIC images were captured every 10 s using a 633 nm HeNe laser. To measure free $Ca^{2+}$ ion concentration, embryos were pre-incubated for 20 min in 5 μM FuraRed-AM (Invitrogen) and FuraRed and DIC images were obtained simultaneously with a 488 nm argon laser. In experiments in which correlations between cytoplasmic movements and developmental potential of the embryos were examined zygotes were imaged in a single plane in transmitted light under standard non-confocal microscopes (Zeiss Axiovert or Deltavision) every 10 s for 2.5 hrs. In experiments in which cytoplasmic movements in the cortex and central parts of zygotes were compared embryos were imaged on the Deltavision microscope in 11 planes every 6 μm, every 10 s for 3 hrs. Optical specifications of all imaging systems used are summarized in Table 7. Intensity of FuraRed fluorescence was measured using ImageJ software. Images were analyzed using custom written software in MATLAB (The Mathworks Inc., Natick, Mass., USA) using algorithms adapted from MatPIV v1.6.1[47]. The algorithm was based on that used in PIV, a standard analysis technique used extensively in fluid dynamics[21-24] that involves cross-correlating image sub-regions between sequential pairs of images. In the PIV analysis each image was divided into square interrogation regions and the cross-correlation coefficient distribution was calculated within a larger region in the next image in the sequence. The peak of the cross-correlation coefficient distribution gave the most likely location in the second image of the material in the interrogation region in the first image. This was then used to calculate the displacement vector over the time between images (FIG. 1A). As the displacement of the pattern of contrast of an area of pixels is being measured over many pixels it is possible to accurately measure sub-pixel movements with this technique[22, 24, 48].

Particle Image Velocimetry (PIV) Analysis

DIC images of fertilized eggs were analyzed using custom written software in MATLAB (The Mathworks Inc., Natick, Mass., USA) using algorithms adapted from MatPIV v1.6.150. The algorithm was based on that used in PIV, a standard analysis technique that involves the use of pattern matching techniques based on cross-correlating sub-regions between sequential pairs of images (see Methods in the main text and FIG. 1*a*). To calculate a displacement for each analysed interrogation region two subsequent PIV iterations were used. First, the displacement was calculated for a larger interrogation area and then it was used as an estimate of where to centre the search area for the next iteration with a smaller interrogation region. The area in which the algorithm looked for the best fit was twice as large as the interrogation region itself. In FIG. 1*a* the figure represents a single iteration of the PIV algorithm. For experiments conducted on Zeiss LSM 510 Meta confocal microscope, an initial interrogation region size of 64×64 pixels was used in the first iteration and then an interrogation region of 32×32 pixels was used in the second iteration. The pixel size for this imaging system was 0.35 μm. For experiments conducted on Zeiss Axiovert and Deltavision microscopes, due to bigger pixel sizes (0.64 and 0.83 μm respectively), in the first iteration an initial interrogation region size of 32×32 pixels was used and then an interrogation region of 16×16 pixels was used in the second iteration. The mean speed of cytoplasmic movement was calculated by taking the mean magnitude of a square of 11 by 11 vectors in the centre of each cell.

Figure 14A:
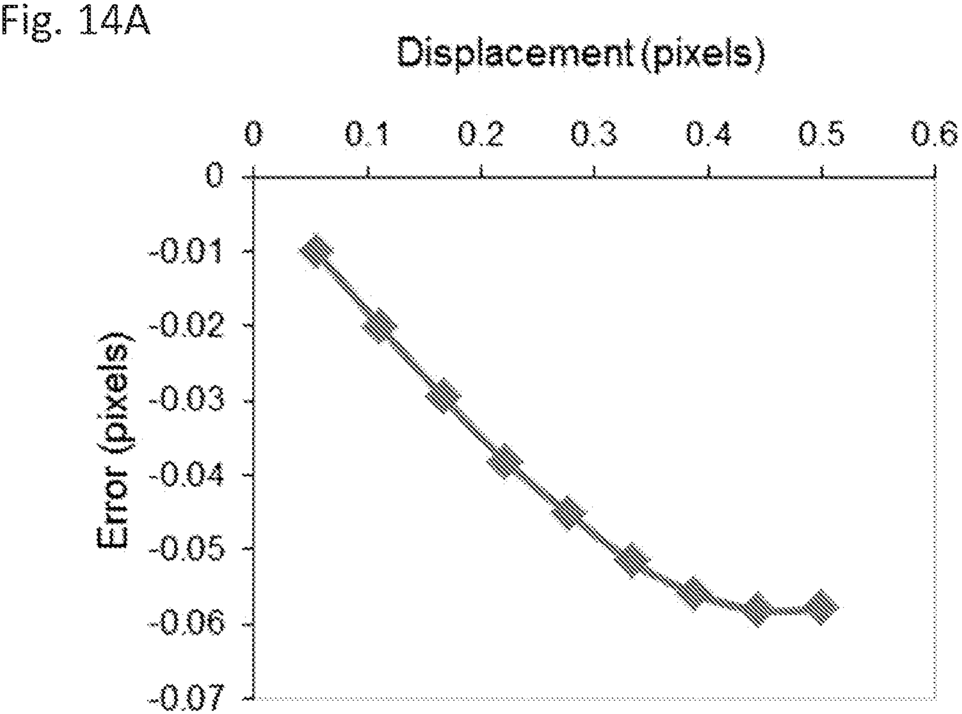
Figure 14B:
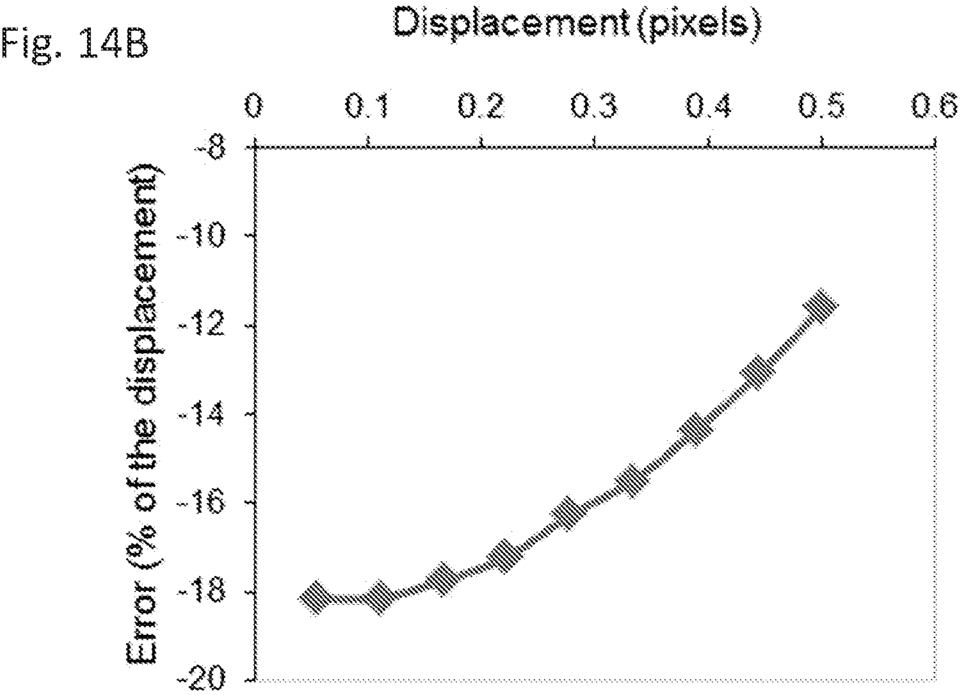

The accuracy of using PIV to measure very small (sub-pixel) displacements, such as observed in the periods between the speed-peaks, was tested by using images of eggs taken at a higher magnification (×252, i.e. objective magnification ×63, digital magnification 4×) and artificially shifting the image and then reducing the magnification and resolution of the image to the same as that used in experiments (×14, i.e. objective magnification ×20, digital magnification 0.7×). The shift was then measured using PIV. It was found that the error was approximately linearly proportional to displacement for displacements of less than approximately 0.3 pixels (FIG. 14), which includes most of the range of the basal movements measured experimentally. This is in agreement with other studies that looked at the accuracy of PIV when measuring small displacements[24, 26, 51]. Displacements of the order of the basal movements (between 0.1 and 0.3 pixels/frame or 3.5-10.6 nm/s for Zeiss LSM 510 Meta, 6.4-19.2 nm/s for Zeiss Axiovert and 8.3-24.9 nm/s for Deltavision) had an error between −18.1% to −15.5% (FIG. 14). As the PIV measurements are being used for comparative purposes these systematic underestimates had little effect on the results or their interpretation.

Analysis of Cytoplasmic Speed and Movement Direction

Figure 1B:
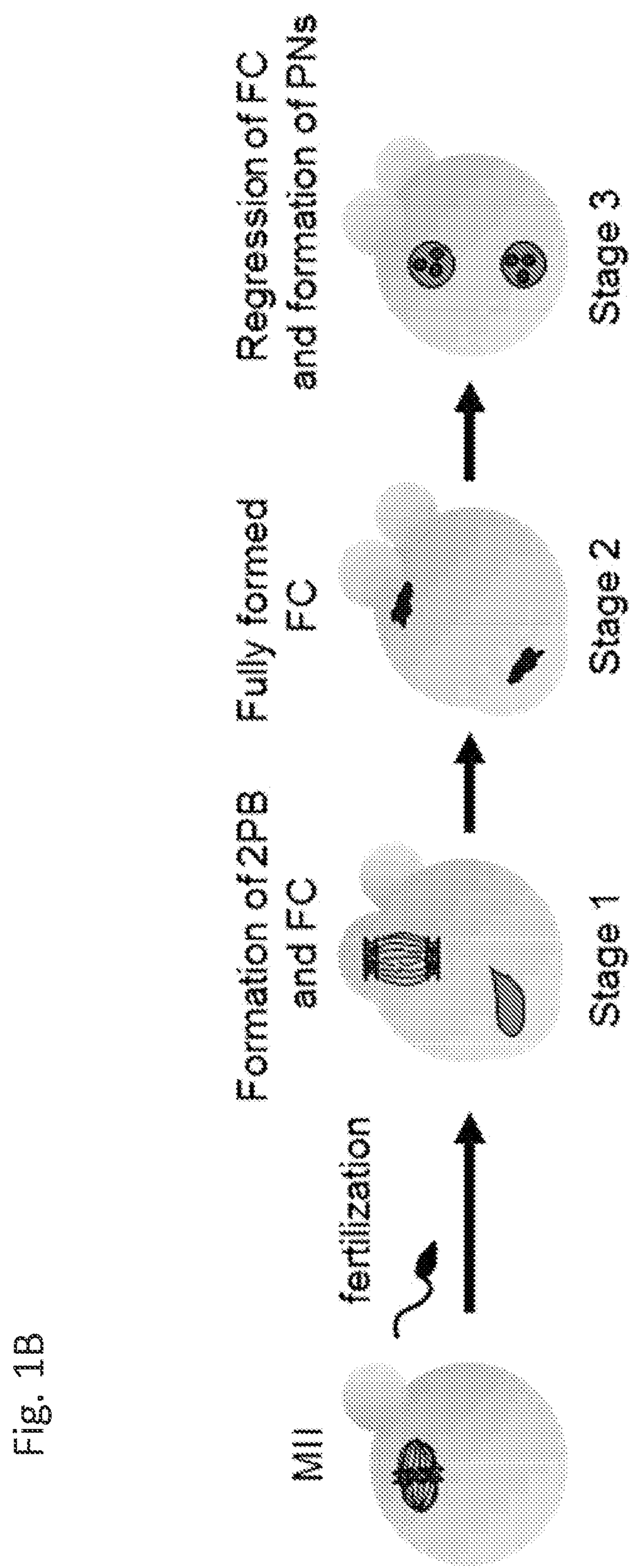
Figure 1C:
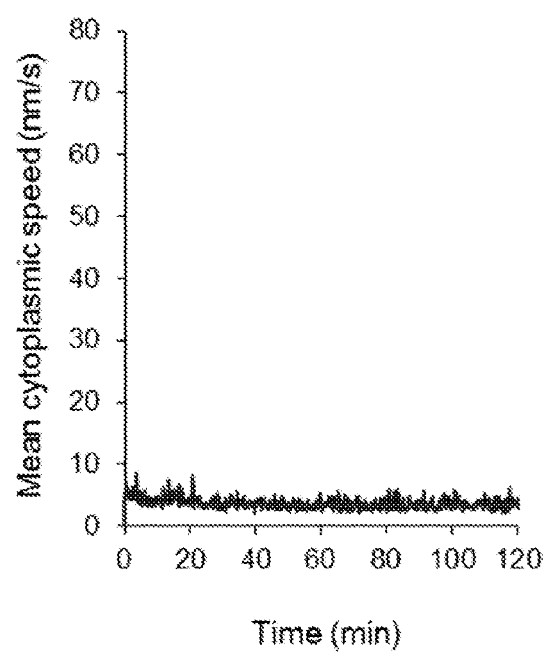
Figure 1D:
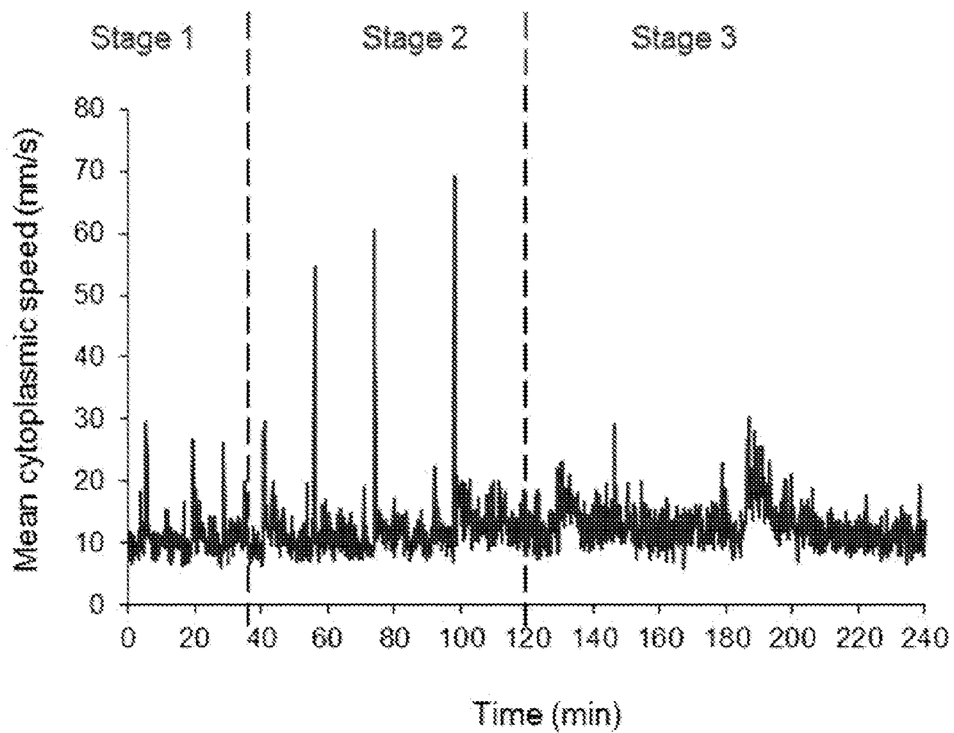

In zygotes that displayed oscillatory changes in the cytoplasmic speed, the mean basal speed was measured in intervals between end of the after-movement and beginning of the subsequent speed-peak or in a period after the last after-movement (FIG. 1D). For zygotes that did not display the speed oscillations, mean basal speed was calculated for whole recording period. In most cases, direction of the cytoplasmic movements was assessed based on the mean vector of all the vectors produced by PIV in the zygote. In some zygotes, vectors formed a pair of vortices and then their common axis was taken as the direction. The direction of highly irregular vector patterns was visually assessed from the direction of the majority of high magnitude vectors.

Intracytoplasmic Sperm Injection

ICSI was carried out as previously described[49] using Leica micromanipulators and Leica inverted microscope. In some experiments heat-inactivated sperm (30 min in 60° C.) was used instead of freshly isolated sperm. The sperm suspension was mixed with M2 medium containing 10% polyvinylpyrrolidone (PVP, Mr=360 kDa). Sperm were delivered into the oocytes' cytosol using a piezo micropipette-driving unit (IntraCel PMAS-CT150, PrimeTech, Japan).

In Vitro Fertilization and Embryo Transfers

To examine a correlation between cytoplasmic movements and developmental potential of the embryos, 10 μl of capacitated sperm suspension was added to eggs surrounded by cumulus cells and then gametes were co-incubated for 2 hrs. In experiments testing specificity of inhibitors or involving live imaging of actin and myosin, prior to fertilization eggs were treated shortly with acidic Tyrode's solution (pH=2.5) to remove zonas, then were mixed with approximately 1 μl of capacitated sperm suspension and incubated together for 30 min. In both cases fertilization was performed in fertilization medium supplemented with 4 mg/ml BSA[45]. Embryos at 2-cell stage were transfer to oviducts of recipient F1 females mated with vasectomised males on 0.5 dpc. They were dissected on 6.5 dpc or 19.5 dpc.

Live Imaging of Actin Filaments and Myosin II

Constructs encoding actin-binding domain of utrophin fused to EGFP (UtrCH-EGFP[26]), myosin II regulatory light chain fused to GFP (MyoRLC-GFP[27]) and protein marker Gap43 tagged with RFP[50] were cloned into a pBluescript RN3P vector and mRNA was synthesized from T3 promotor using mMessage mMachine T3 kit (Ambion). mRNAs (pipette concentration 0.5 μg/μl for UtrCH-EGFP and MyoRLC-GFP and 0.36 μg/μl for Gap43-RFP) were injected into GV oocytes that were subsequently cultured for approximately 5 hrs in M2 with 150 μg/ml dbcAMP and then washed out and transferred to M16 medium to mature. Oocytes that 16 hrs later achieved MII stage were selected for in vitro fertilization and then were imaged every 10-15 s on an inverted spinning disc confocal microscope (Zeiss). UtrCH-EGFP, MyoRLC-GFP and Gap43-RFP fluorescence intensities were measured in the FC cortex and in the cytoplasm using ImageJ software. Values obtained for cortical UtrCH-EGFP, MyoRLC-GFP and Gap43-RFP were standardised with respective intensities obtained for the cytoplasm to eliminate any intensity changes that were caused by imaging artefacts, e.g. fluctuations in laser power. The final results were then presented as ratios between UtrCH-EGFP and Gap43-RFP or MyoRLC-GFP and Gap43-RFP standardised intensities to eliminate any intensity changes caused by shifts in focus.

Immunostaining

Embryos were fixed in 4% PFA and permeabilised as described before[41]. Embryos were scanned using an inverted confocal microscope (Zeiss LSM 510 Meta).

In more detail, embryos were fixed in 4% PFA (30 min, RT or 4° C. overnight), permeabilised with 0.2-0.5% Triton-X100 (30 min, RT) and blocked with 3% BSA or 10% FCS. Subsequently, they were stained with following antibodies and dyes:

1) mouse anti-tubulin beta antibody labeled with FITC (Sigma-Aldrich; dilution 1:50 in 3% BSA 1.5 h at RT);

2) mouse anti-actin beta antibody (Sigma-Aldrich; dilution 1:100 in 3% BSA 1.5 h at RT)

3) goat anti-Gata4 primary antibody (Santa Cruz; 1:200 in 10% FCS, overnight in 4° C.) followed by a secondary antibody labeled with AlexaFluor 568 (Molecular Probes; 1:1000 in 10% FCS, 1.5 h at RT);

4) phalloidin labeled with TexasRed or OregonGreen (Invitrogen; 1:100, 30 min, RT or overnight, 4° C.);

5) Hoechst 33342 (Molecular Probes; 100 ng/ul in PBS, 30 min, RT or overnight, 4° C.).

Embryos were scanned using an inverted confocal microscope (Zeiss LSM 510 Meta).

Statistical Analysis

Statistical analyzes were performed ether using Student's t-test, chi-squared test or appropriate regression models. Because of the sequential nature of the experiments performed and the a priori nature of the questions that we sought to address, we assessed statistical significance at the 5% level. To determine relationships between mean basal speed or mean interval between speed peaks and the total number of cells produced after 4 days of development (i.e. the four-day cell count), we fitted negative-binomial models to the cell counts of the embryos, with a logarithmic link function relating the mean cell count to the linear combination of explanatory variables: the mean basal speed, the square of mean basal speed, the mean interval between speed peaks, the square of the mean interval between speed peaks, and the various interactions between the basal speed and speed peaks variables. In our initial analysis we took into account the potential confounding effects of the imaging system used (Zeiss or Deltavision) on embryo development. However since we found that the interaction between the analyzed parameters, the quadratic effect of the mean interval between speed-peaks and the image system, were not statistically significant and did not contribute any further explanatory power, we dropped them in our final analysis. The likelihood ratio test of the full model with all the variables mentioned above included in comparison with the final model yielded a non-statistically significant change in the log-likelihood (p=0.53). Negative-binomial modeling of the cell count was chosen over the more standard Poisson regression modeling of the cell count to account for variation observed in the cell count data[51].

To investigate the relationship between the same explanatory variables as described above and the probability that a zygote develops into a blastocyst (i.e. achieves at least 32-cell stage), we also analyzed our data by fitting logistic regression models after dichotomizing total number of cells produced after 4 days of development into a binary variable indicating whether or not the total cell count exceeded 31 cells. The final logistic model included the same explanatory variables as those in the final negative-binomial model. (The likelihood ratio test of the full model against the final model yielded a non-statistically significant change in the log-likelihood (p=0.30).

Example 1

Fertilization of the Mouse Egg Results in Bursts of Rhythmic Cytoplasmic Motion To characterise cytoplasmic movements upon fertilization of the mouse egg and to evaluate whether, and if so how, they relate to other events associated with fertilization we first filmed eggs from the time immediately after fertilization until pronuclei formation. We then used advanced image analysis based on the PIV method[21-24] to analyse and quantify these movements (FIG. 1A). This revealed that fertilization of the mouse egg was followed by dramatic periodic increases and decreases in velocity of the cytoplasmic movements (that we termed speed-peaks; FIG. 1B-D, n=55 unfertilized oocytes and n=125 eggs fertilized in vivo). This sequence of fast repetitive movements throughout the egg cytoplasm lasted for approximately 4 hours, until pronuclei formation. The speed-peaks were initially of relatively low amplitude (between anaphase of meiosis II and early FC outgrowth; Stage 1); but subsequently developed significantly greater amplitudes when the FC fully extended (Stage 2). Finally, their amplitude decreased during and following FC regression (Stage 3) (FIG. 1B, D, Table 1). In Stage 2 the rapid cytoplasmic movements were greatest in the plane bisecting the FC equatorially and became slower in the more peripheral planes (FIG. 9). The PIV analysis revealed that each speed-peak was followed by after-movements that usually persisted for more than 4 mins and were of lower amplitude. Movements during Stage 3 were exceptions to this rule in that the speed-peaks were often less distinct than the after-movements (FIG. 1D, Table 1). Moreover, we noticed that fertilization led to greater than 2-fold increase in the basal mean cytoplasmic speed (the speed during inter-peak intervals or after the last recorded peak) in comparison to the resting level of unfertilized oocytes (FIG. 1C-D, Table 2).

Figure 1E:
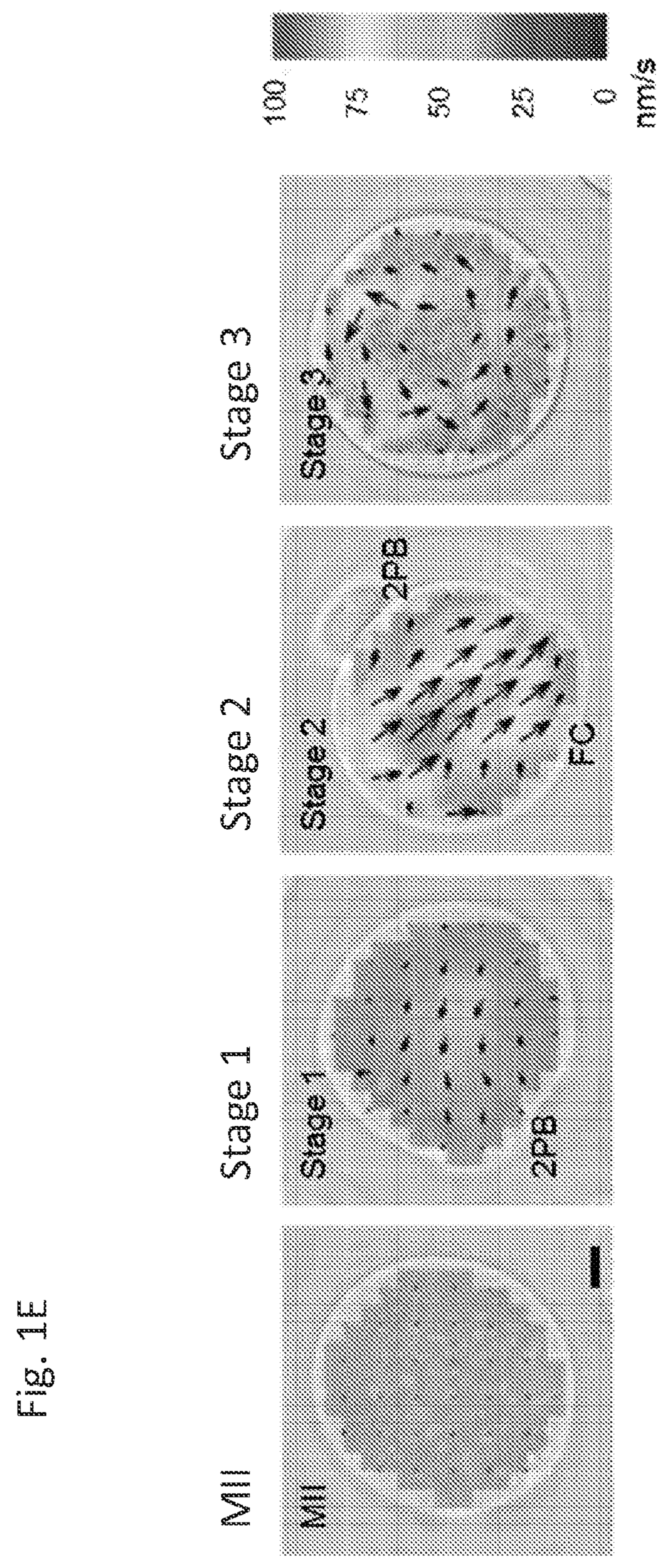

Our analysis revealed that during Stage 1, the vectors of these abrupt cytoplasmic movements tended to be towards the developing second PB (17/25 speed-peaks, 11 zygotes). This directionality changed during Stage 2 such that the vectors were directly towards the FC or sometimes slightly displaced towards the second PB (64/65 speed-peaks, 19 zygotes). There was no persisting pattern during the low magnitude after-movements or inter-peak intervals in either of these stages. At Stage 3 directionality or any pattern of the speed-peaks was not any longer apparent (FIG. 1E, Table 4). These speed-peaks ceased after FC regression when pronuclei were observed in the majority of zygotes (49/63, 77.8%) (FIG. 1D). Thus, our results indicate that fertilization of the mouse egg triggers speed peaks of cytoplasmic movements that at their strongest are directed towards the FC forming above the site of sperm entry.

Example 2

Figure 2A:
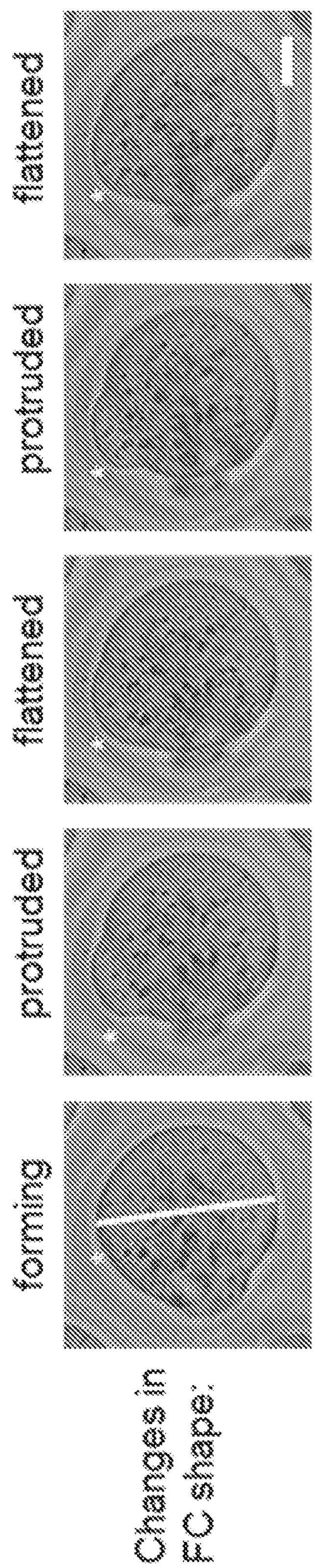
Figure 2B:
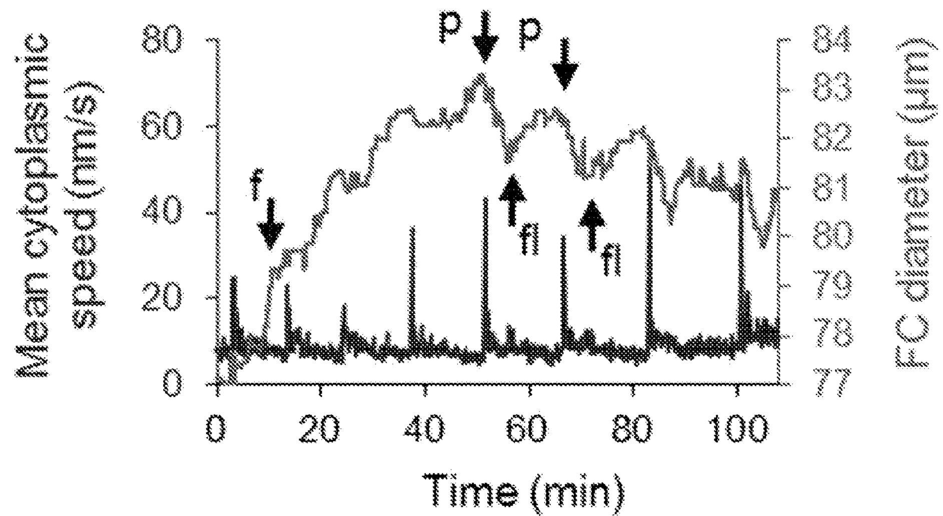
Figure 2C:
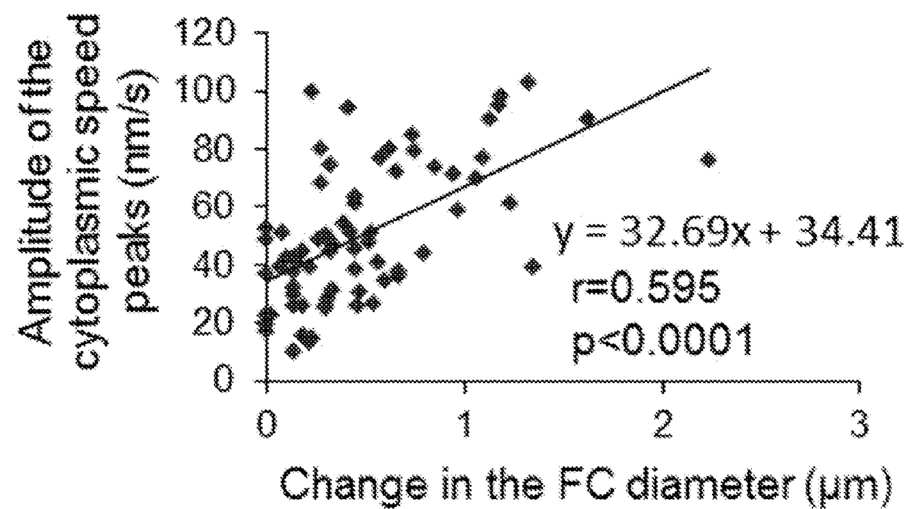

High Amplitude Cytoplasmic Speed-Peaks Correlate with Pulsations of the FC and Depend on the Actomyosin Cytoskeleton Since the direction of the abrupt movements at Stage 2 suggested that the FC could be involved in their generation, we next examined the morphology of the FC throughout this period (69 speed-peaks, 14 zygotes). This showed that at each speed-peak, the apex of the FC sank inwards and the region where the FC merged into the convex outline of the zygote widened. As a consequence, the diameter of the zygote along the axis of the FC (hereinafter called the 'FC-diameter') decreased by 1.28+/−0.66 μm (1.55+/−0.79% of its length) (FIG. 2A, C). The shape of the FC was restored during the inter-peak interval (FIG. 2C). Interestingly, the extent of reduction of the FC diameter showed a linear association with speed-peak amplitude (20 zygotes, 71 speed-peaks analyzed) (FIG. 2B).

Figure 2D:
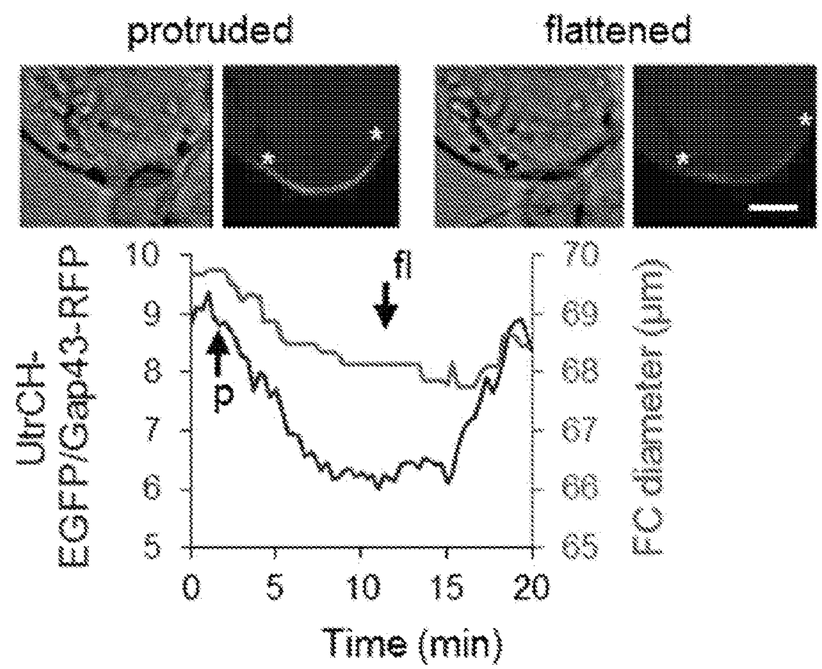
Figure 2E:
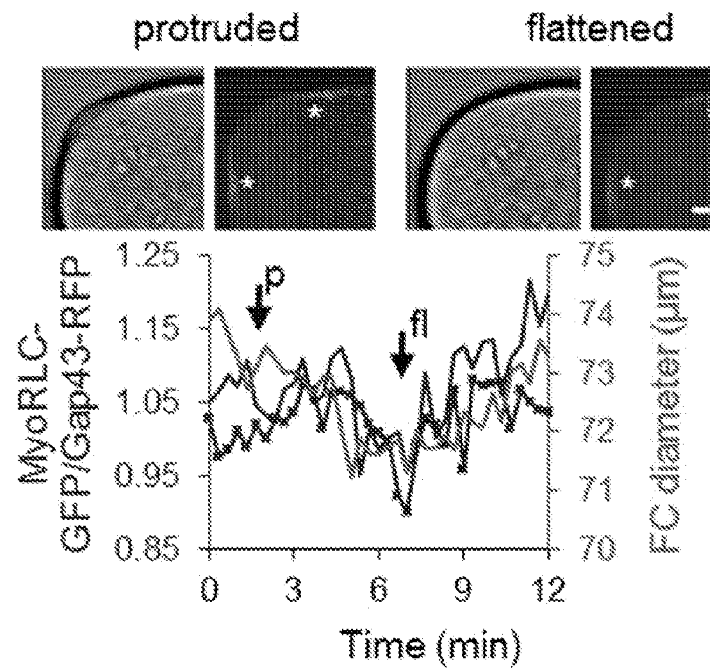
Figure 10:
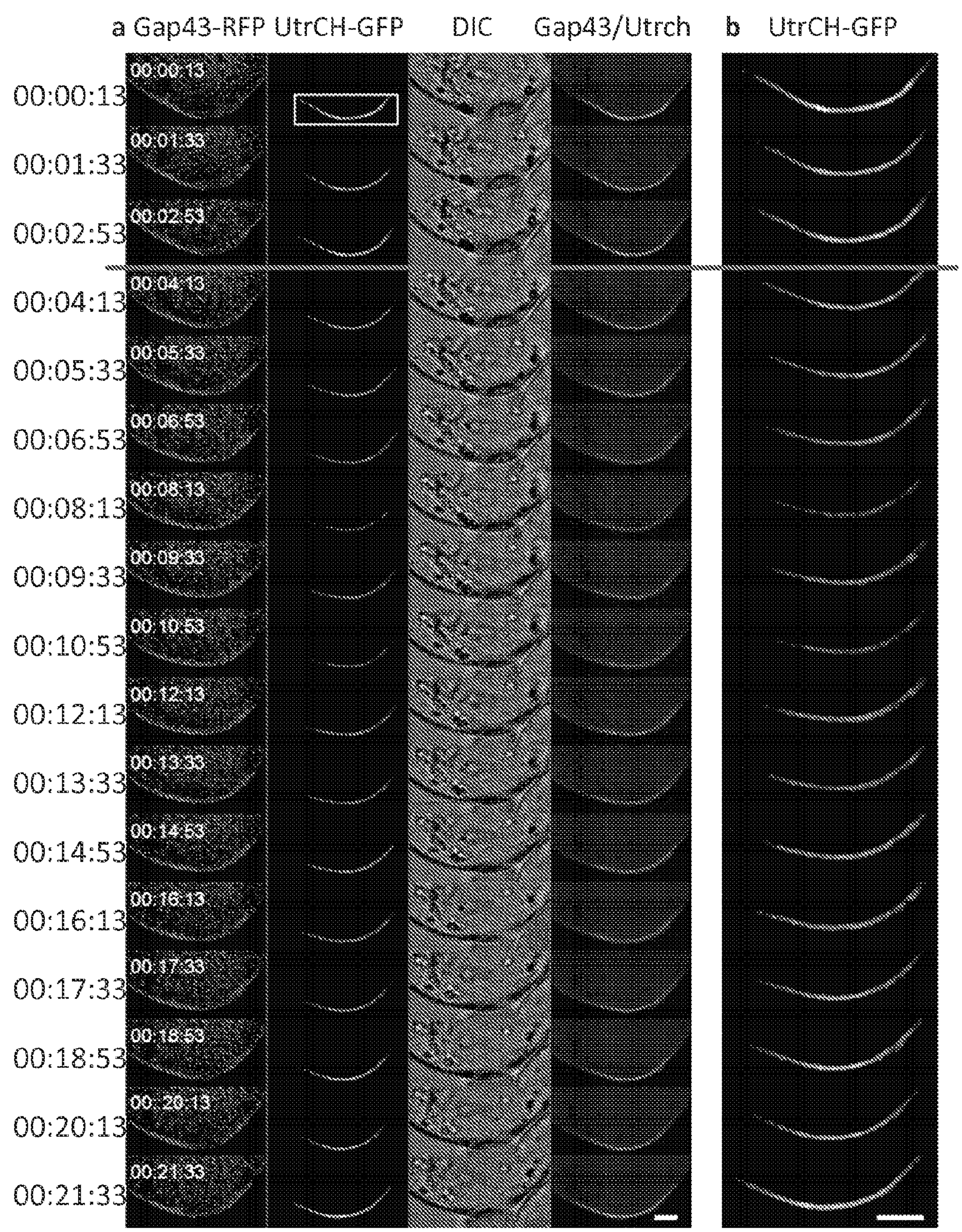
Figure 11:
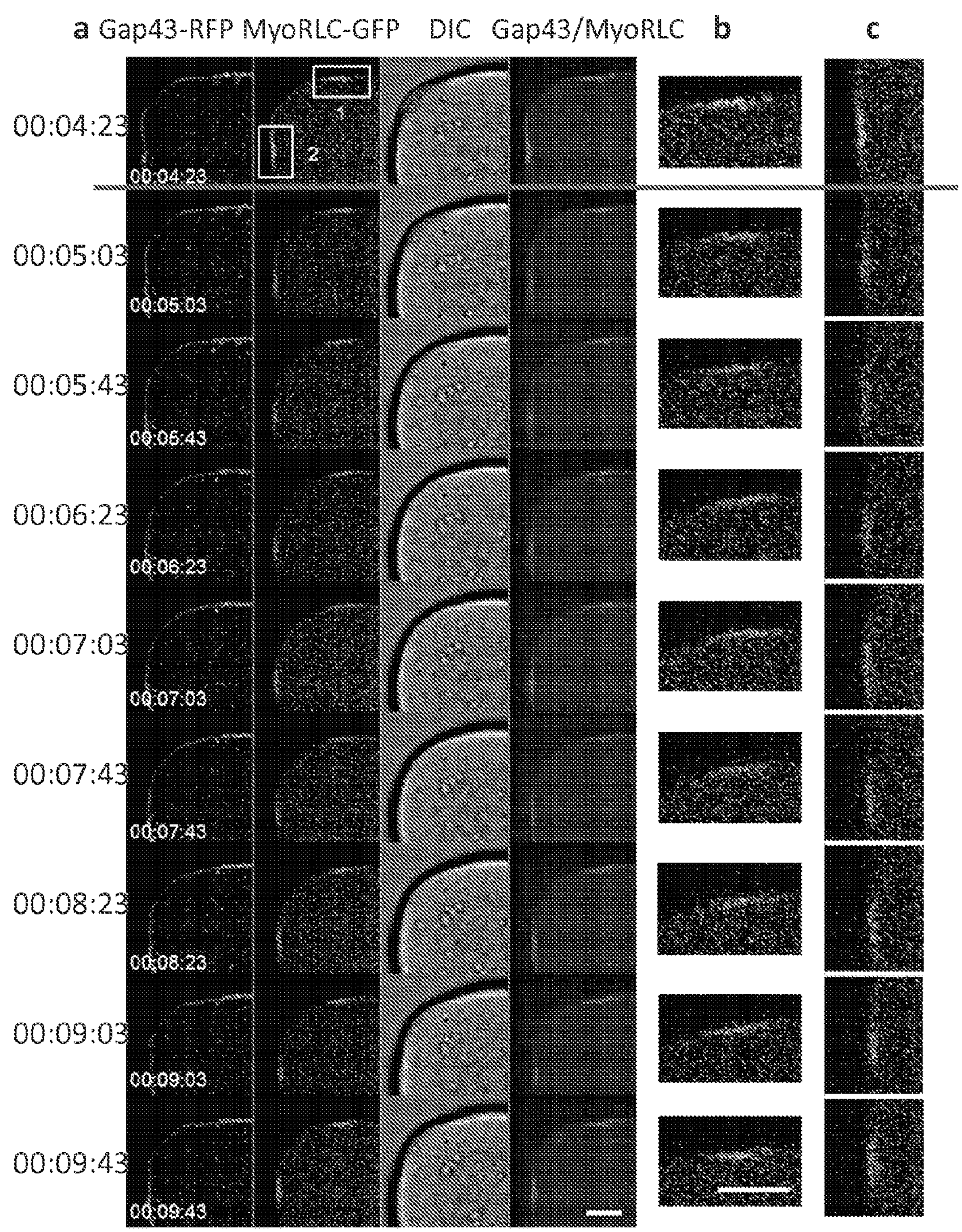

Since the actomyosin cytoskeleton is enriched in the FC region[17, 25], we considered that this might be responsible for FC pulsations. To evaluate this possibility, we visualized actomyosin throughout these pulsations by injecting oocytes with mRNAs encoding either the actin-binding domain of utrophin tagged with EGFP (UtrCH-EGFP[26]) or the regulatory light chain of myosin II tagged with GFP (MyoRLC-GFP[27]). Measurements of the mean fluorescence intensity of UtrCH-EGFP in such oocytes after their fertilization revealed oscillatory changes in the continuous actin layer underlying the FC; the fluorescence intensity of the actin marker decreased as the FC relaxed and increased as the FC was gradually protruding (FIG. 2D, FIG. 10). Similar results were obtained for the mean fluorescence intensity of MyoRLC-GFP underlying the FC shoulders (FIG. 2E, FIG. 11). Such fluctuations in UtrCH-EGFP and MyoRLC-GFP fluorescence might reflect a change in the amount of the actomyosin in that region. However, since these changes are relatively small, transient and repetitive, it is more likely that they represent contractility of actomyosin encircling the FC leading to its pulsations.

Figure 2F:
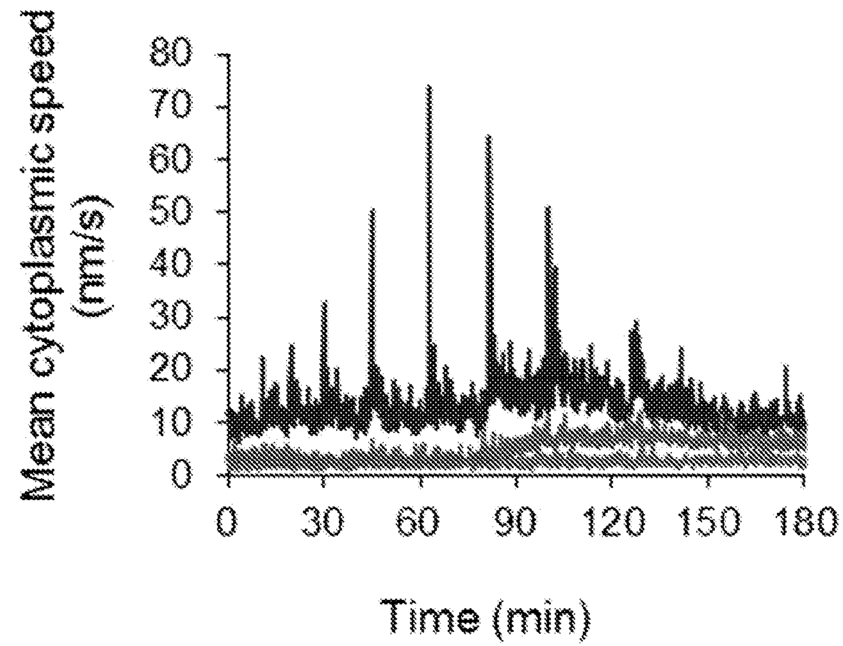
Figure 2G:
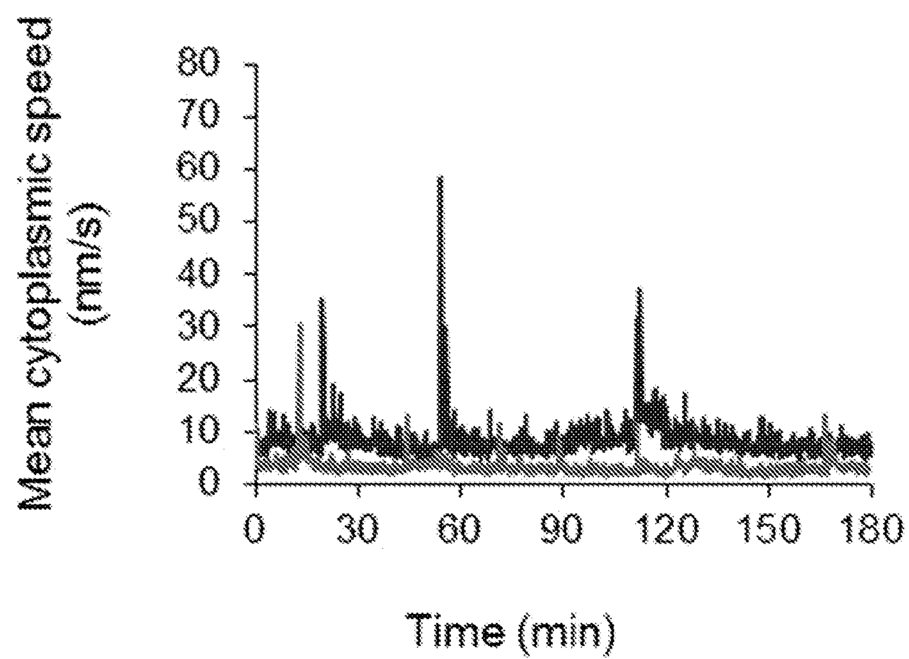
Figure 12:
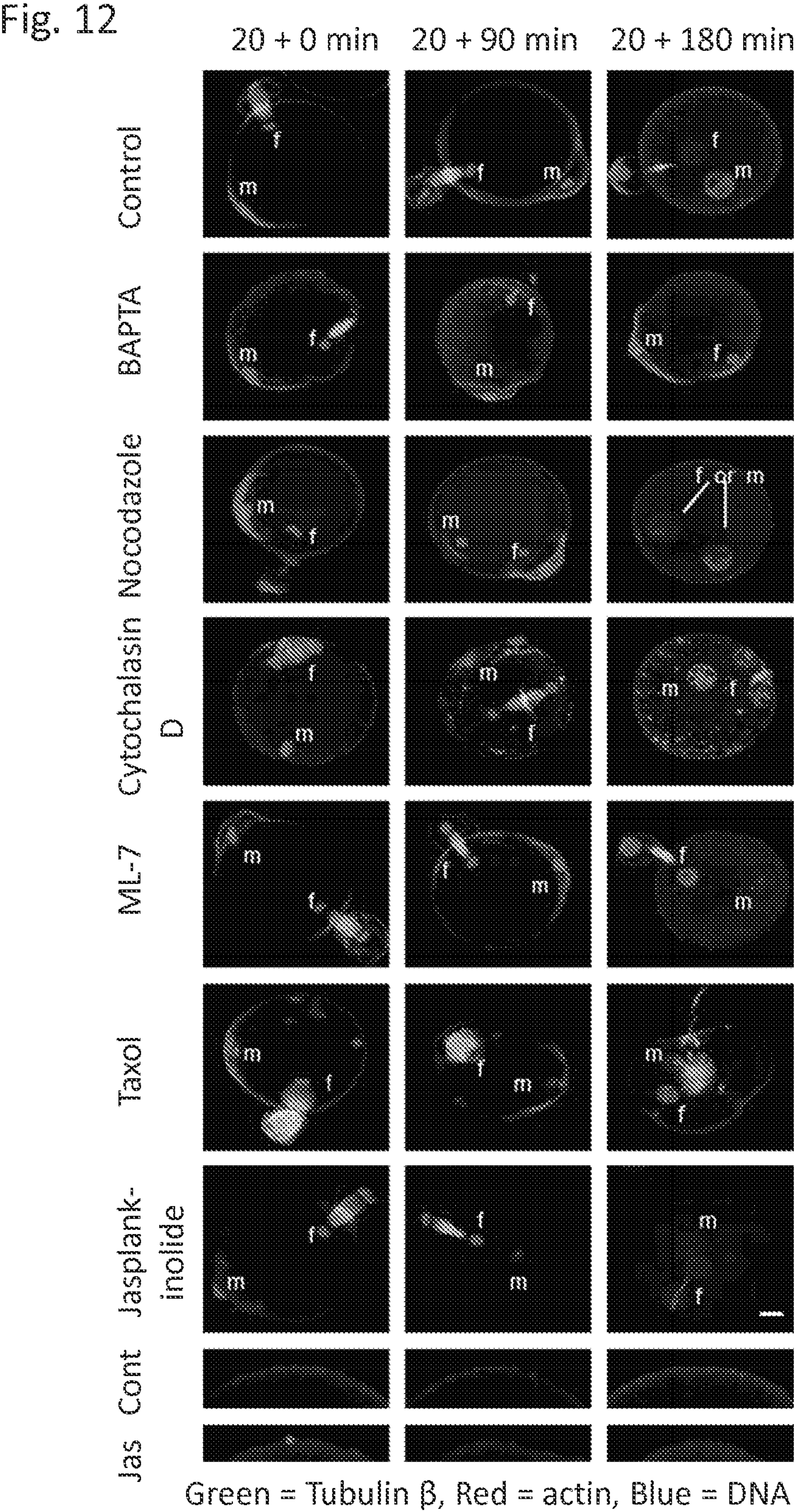

As FC movements occurred in frame with the cytoplasmic speed peaks directed towards the FC, we next examined whether the actomyosin cytoskeleton was responsible for both. To this end, we used selective inhibitors to interfere with both the actomyosin and microtubule cytoskeletons. Their specificity was confirmed by immunostaining (FIG. 12) and their effect on cell cycle progression is presented in Table 5. We found that neither nocodazole-induced depolymerisation nor taxol-induced stabilisation of microtubules inhibited speed-peaks although their dynamics were slightly changed. Nocodazole treatment increased cytoplasmic speed in some after-movements and in all intervals between speed-peaks (n=38, FIG. 2F, Table 1, 2), whereas taxol treatment decreased the amplitude of speed-peaks, some after-movements and cytoplasmic speed in all inter-peak intervals (n=27, FIG. 2G, Table 1, 2). In contrast, actin depolymerisation with cytochalasin-D or stabilisation of actin filaments with jasplakinolide resulted in an almost 3-fold decrease in basal speed (FIG. 2F, G, Table 2). Moreover, cytochalasin-D treatment dramatically abolished speed-peaks (FIG. 2F). Only in 2 out of 21 analyzed zygotes (9.5%) were unfocused, low-amplitude speed-peaks recorded. Speed-peaks were still present in jasplakinolide-treated zygotes (n=60) although their amplitudes were significantly lower than in controls and after-movements were virtually undetectable (FIG. 2G, Table 1). In almost all zygotes, treatment with ML-7, a myosin light chain kinase (MLCK) inhibitor, also blocked cytoplasmic speed oscillations (16/17 zygotes, 94.1%) (FIG. 2F), and only a single exceptional zygote displayed indistinct low amplitude speed-peaks.

These experiments also revealed that depolymerisation or stabilisation of microtubules, by respective treatments with nocodazole or taxol, had no effect upon either formation and/or maintenance of the FCs. By contrast, FCs did not form in the majority (20/21, 95%) of zygotes treated with cytochalasin-D in agreement with previous studies[13]. Stabilisation of actin filaments in zygotes treated with jasplakinolide still permitted formation and/or maintenance of FCs, but they were not as prominent as in controls. FCs were present in just over half of embryos (10/17, 58.8%) when MLCK activity was inhibited and when present, they were less well developed. This accords with the previous conclusion that MLCK activity is involved in formation and maintenance of the FC[25, 28]. Together these results indicate that both the cytoplasmic oscillations and FC pulsations depend primarily on the actomyosin cytoskeleton.

Example 3

Cytoplasmic Movements Correlate with and Depend on $Ca^{2+}$ Transients

Figure 3A:
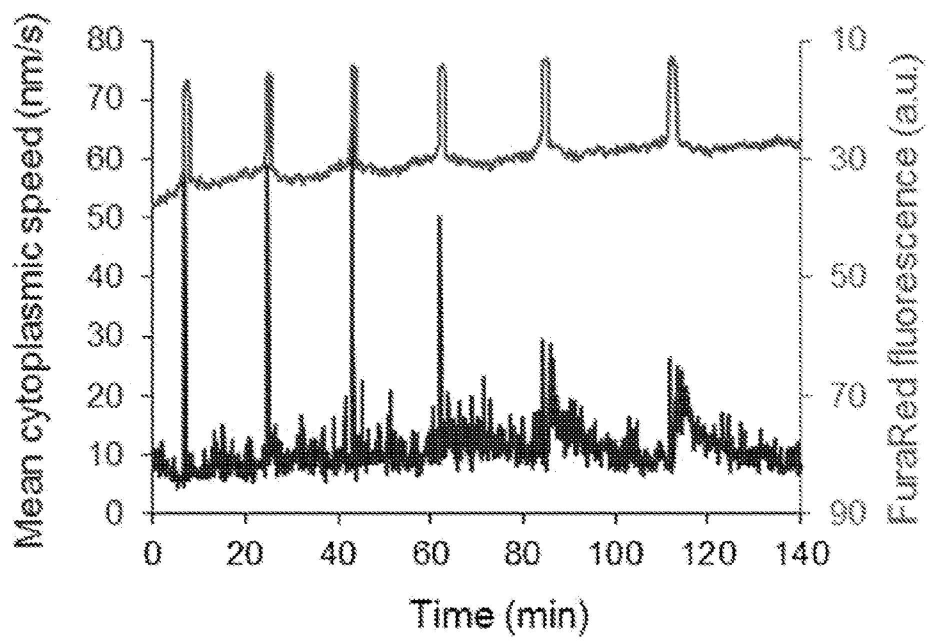

As fertilization is known to initiate oscillations of free $Ca^{2+}$ [10, 29], we next wished to address whether the actomyosin-mediated speed-peaks might depend upon these $Ca^{2+}$ pulses. To this end, we loaded fertilized eggs with the $Ca^{2+}$ sensitive fluorescent dye FuraRed, and simultaneously collected FuraRed fluorescence and DIC images. In 32 zygotes, all 121 speed-peaks were accompanied by an increase in $Ca^{2+}$. The cytoplasmic speed increased exactly (within the resolution of our recording interval) as $Ca^{2+}$ levels peaked (FIG. 3A). Only in a single zygote with unusually frequent $Ca^{2+}$ oscillations were some $Ca^{2+}$ spikes (4/17) not mirrored by speed-peaks. In some eggs fertilized by ICSI we managed to record speed-peaks accompanying the first $Ca^{2+}$ transient. They were of higher amplitude than the rest of Stage 1 speed-peaks (FIG. 9) corresponding to the first $Ca^{2+}$ transient being bigger than subsequent ones.

Figure 3B:
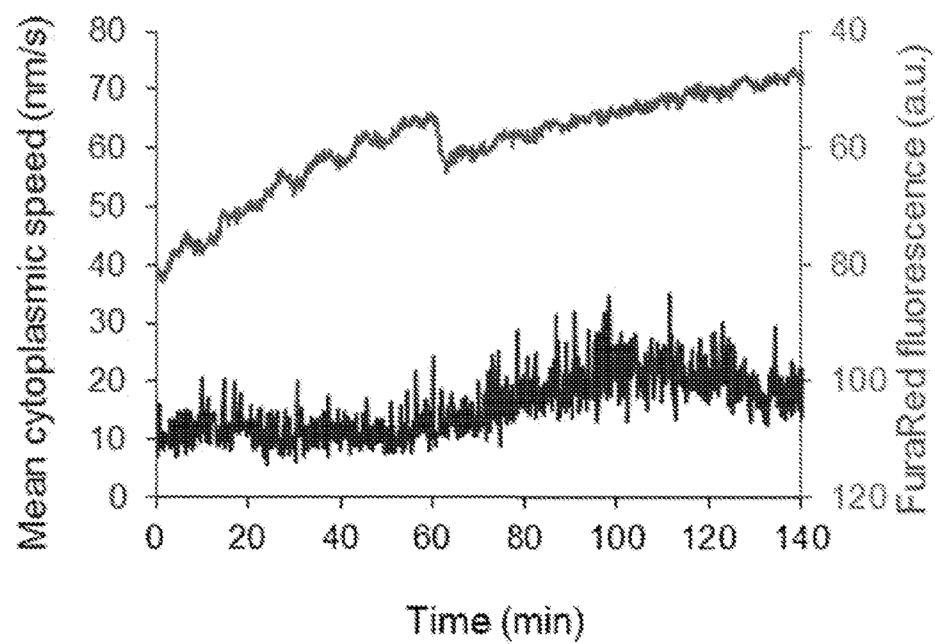

To determine if $Ca^{2+}$ oscillations are essential for cytoplasmic movements, we recorded motion in 21 fertilized eggs loaded with the $Ca^{2+}$ chelator BAPTA, known to inhibit calcium oscillations without changing the basal level of intracellular $Ca^{2+}$ [30]. This treatment suppressed high amplitude speed-peaks but elevated the mean basal cytoplasmic speed to 1.7-fold more than controls (FIG. 3B). Although BAPTA disrupted microtubules (FIG. 12), as observed in other systems[31, 32], this was unlikely to be responsible for the loss of speed-peaks because specific disruption of microtubules did not cause a similar phenotype (see above).

Figure 3C:
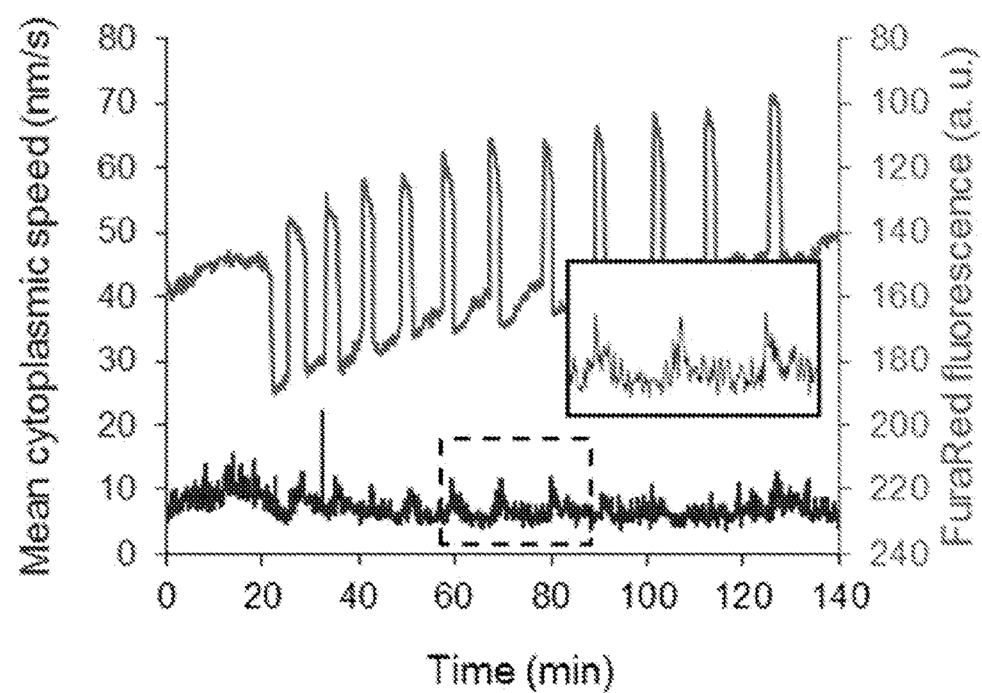

Interestingly, when we activated mouse eggs (n=47) using $SrCl_2$, thus causing $Ca^{2+}$ oscillations similar to those seen after fertilization, only 30% (133/444) of $Ca^{2+}$ transients were accompanied by speed peaks. Moreover these did not resemble the speed peaks of zygotes as they had very low amplitudes (FIG. 3C, Table 1, 3) and also were often delayed by 10-30 s with respect to the onset of the $Ca^{2+}$ transient. After-movements were present with 76.8% (341/444) of these Sr-induced $Ca^{2+}$ transients, but their amplitudes were also lower than in zygotes (Table 1, 3). This suggests that although $Ca^{2+}$ oscillations are necessary for the rapid cytoplasmic movements, they are not sufficient to trigger distinct high-amplitude speed-peaks. Thus, fertilization leads to additional events that fully enable these motions.

Example 4

Functional Sperm Proteins are Required to Initiate Cytoplasmic Movements

Figure 4A:
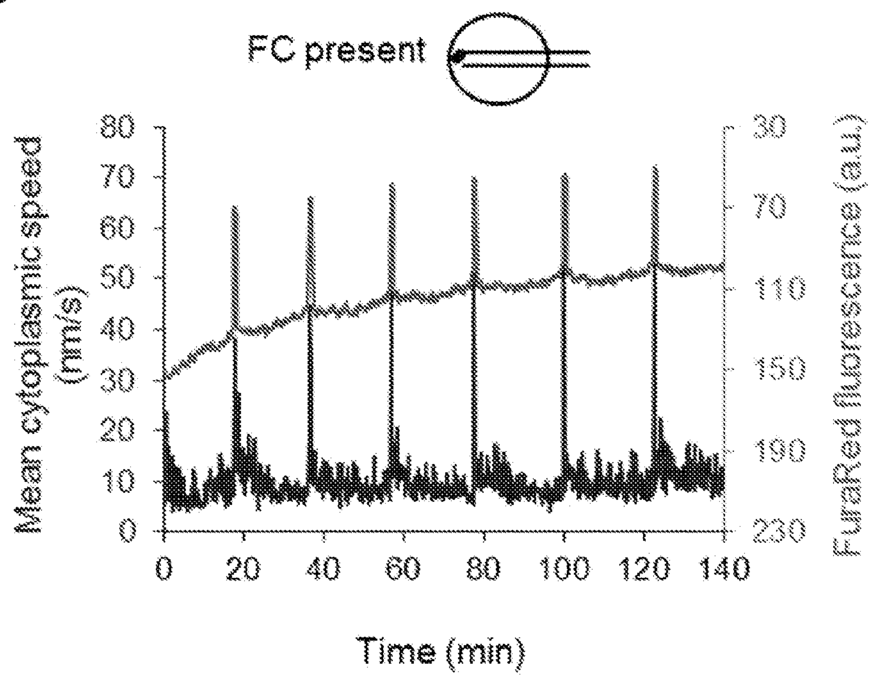
Figure 4B:
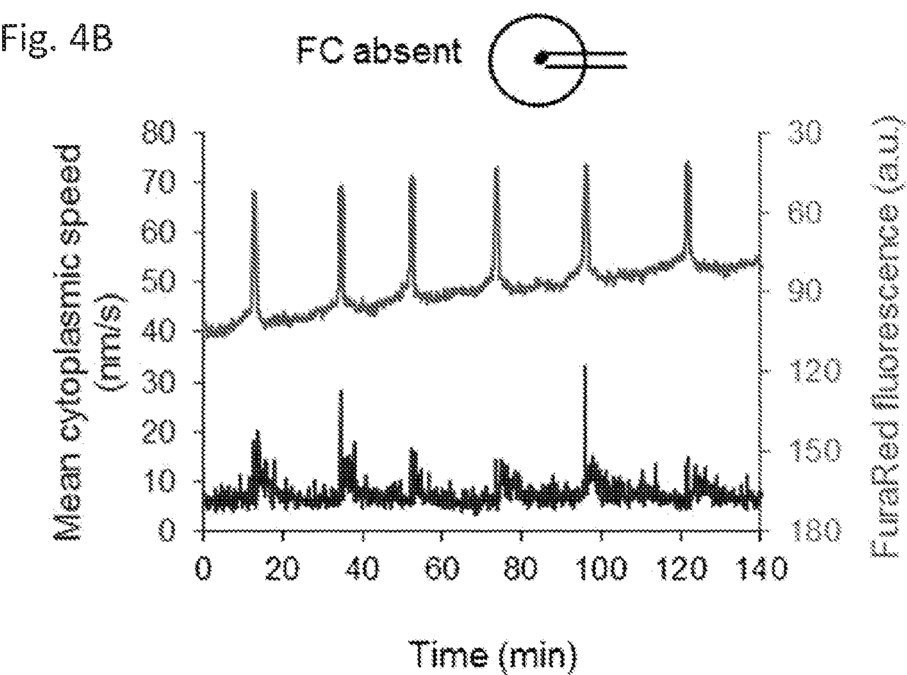

To further characterize the relative contribution made by either the sperm per se or the FC upon both cytoplasmic speed-peaks and $Ca^{2+}$ oscillations, we injected sperm directly into the egg, either immediately under the cortex or into the center of the cell. Since formation of the FC depends on interplay between sperm chromatin and cortical actin and is distance-dependent[33], FCs were only formed in the former group of injected eggs. In both cases the injected sperm resulted in $Ca^{2+}$ oscillations and egg activation. However, whereas in eggs that formed FCs, 97% (101/104) of $Ca^{2+}$ transients were accompanied by speed-peaks (n=17, FIG. 4A), in eggs without FCs, 71% (207/290) of $Ca^{2+}$ transients had speed-peaks (n=35; FIG. 4B). Importantly, the mean amplitude of speed-peaks was significantly lower in eggs without FCs, whereas in eggs with FCs amplitudes were similar to those in naturally fertilized ones (FIG. 4AB, Table 1, 3). However, the mean amplitude of speed-peaks during pronuclei formation and of the after-movements from all stages were similar in both groups (Table 3), suggesting that mechanism of these particular movements may be FC-independent.

Figure 4C:
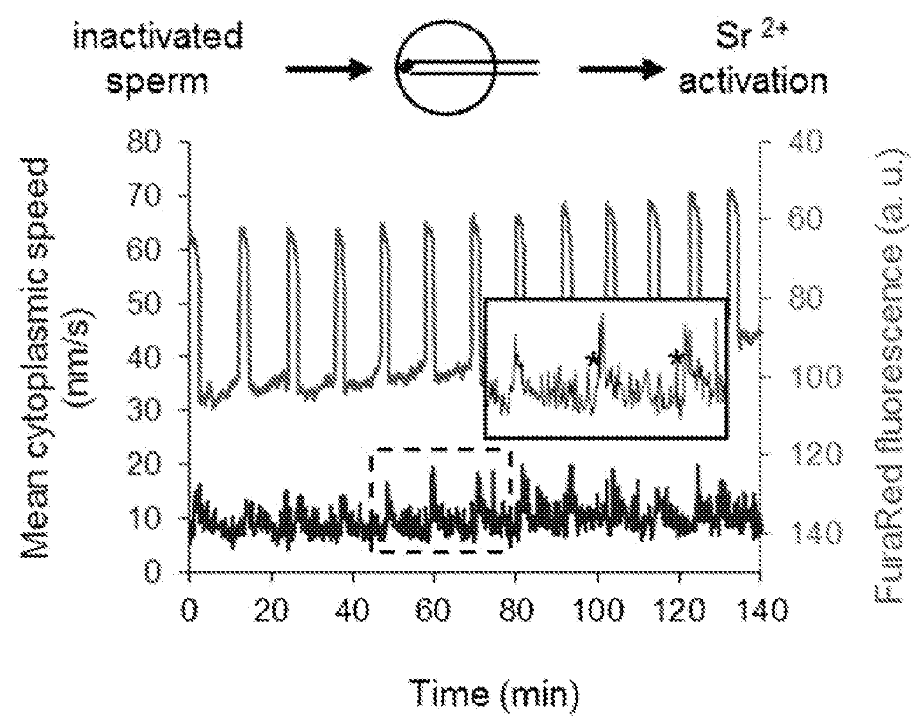
Figure 4D:
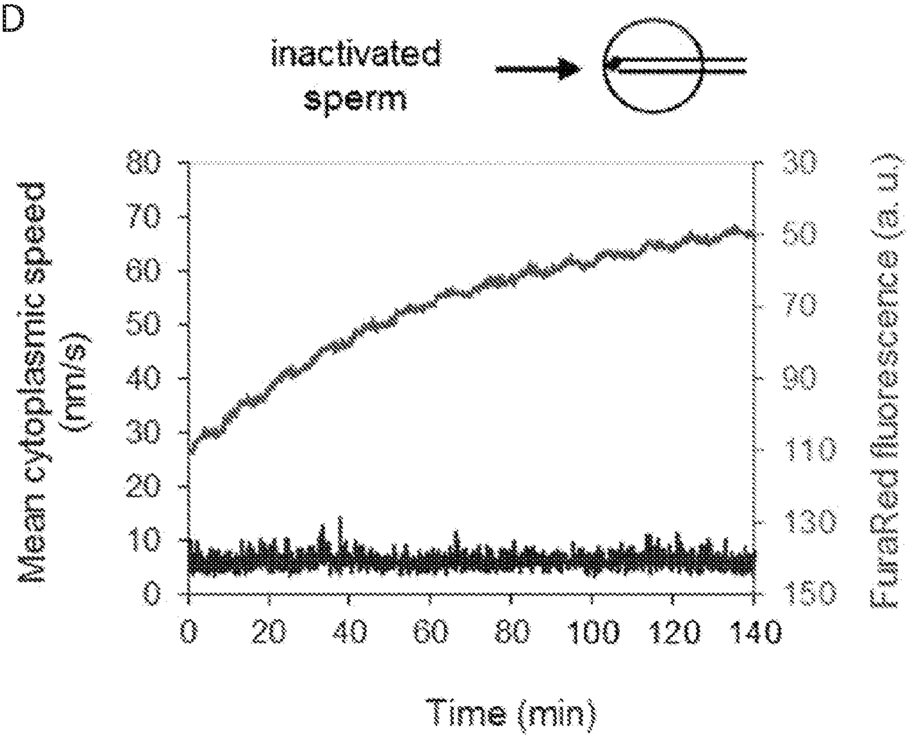

To further dissect the contribution of FCs to the triggering of cytoplasmic movements, we examined if speed-peaks would occur in response to injection of heat-inactivated sperm heads that are devoid of all functional proteins and serve as a source of DNA. Association of chromatin with the cortex is known to be sufficient to trigger FC-like formation[33]. Consequently when heat-inactivated sperm heads were injected into the cortex and eggs activated by $Sr^{2+}$, both $Ca^{2+}$ oscillations and FC formation were observed. In such zygotes (n=25), 60.8% (48/79) of $Ca^{2+}$ transients were accompanied by speed-peaks when the FCs were present (Stage 2). However, speed-peak amplitudes remained relatively low (FIG. 4C, Table 3). Interestingly, the FC pulsations were also much less pronounced than those observed in normal zygotes and neither speed-peaks nor FC pulsations were perfectly synchronized with the peaks of $Ca^{2+}$ transients but occurred 10-30 s later. No $Ca^{2+}$ oscillations were recorded in eggs injected with inactivated sperm and left without parthenogenetic activation (FIG. 4D). Together these results suggest that high amplitude speed-peaks are associated with FC pulsations and are facilitated by functional proteins of the sperm.

Example 5

Cytoplasmic Movements Provide an Indicator of Embryo Vitality

Figure 5A:
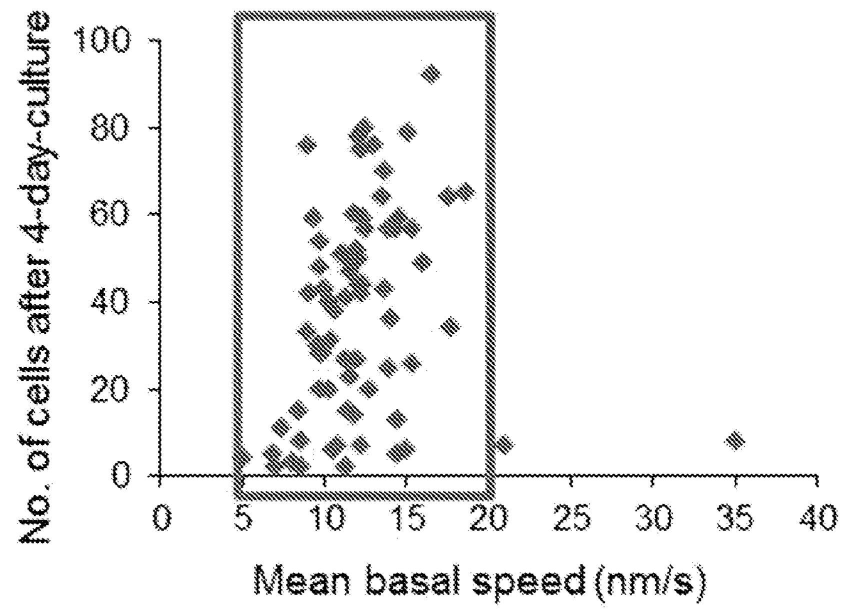
Figure 5B:
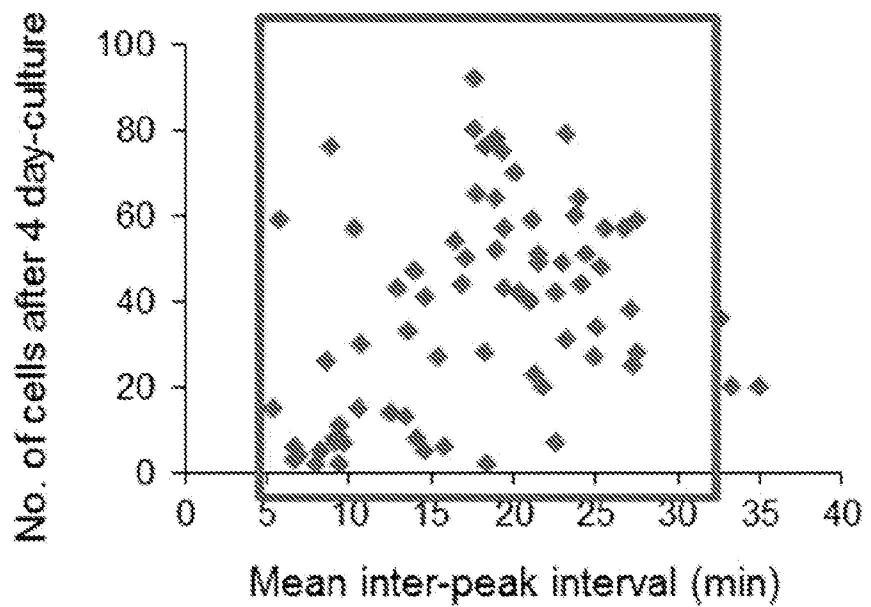
Figure 5C:
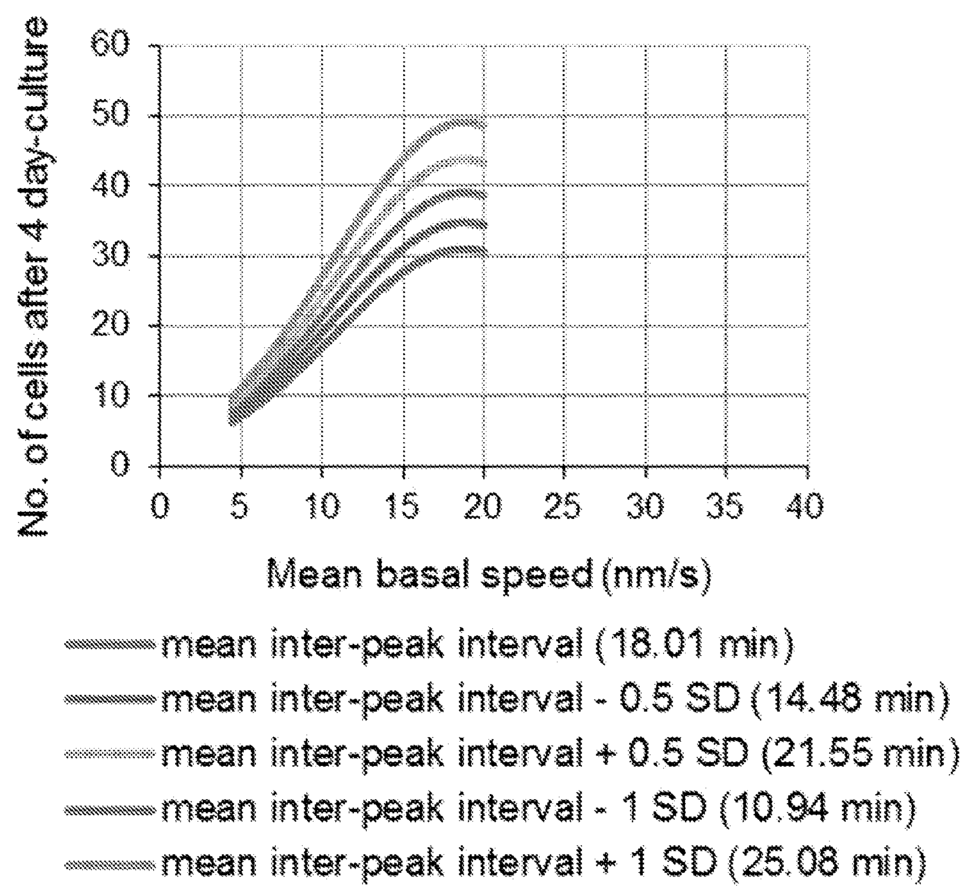
Figure 5D:
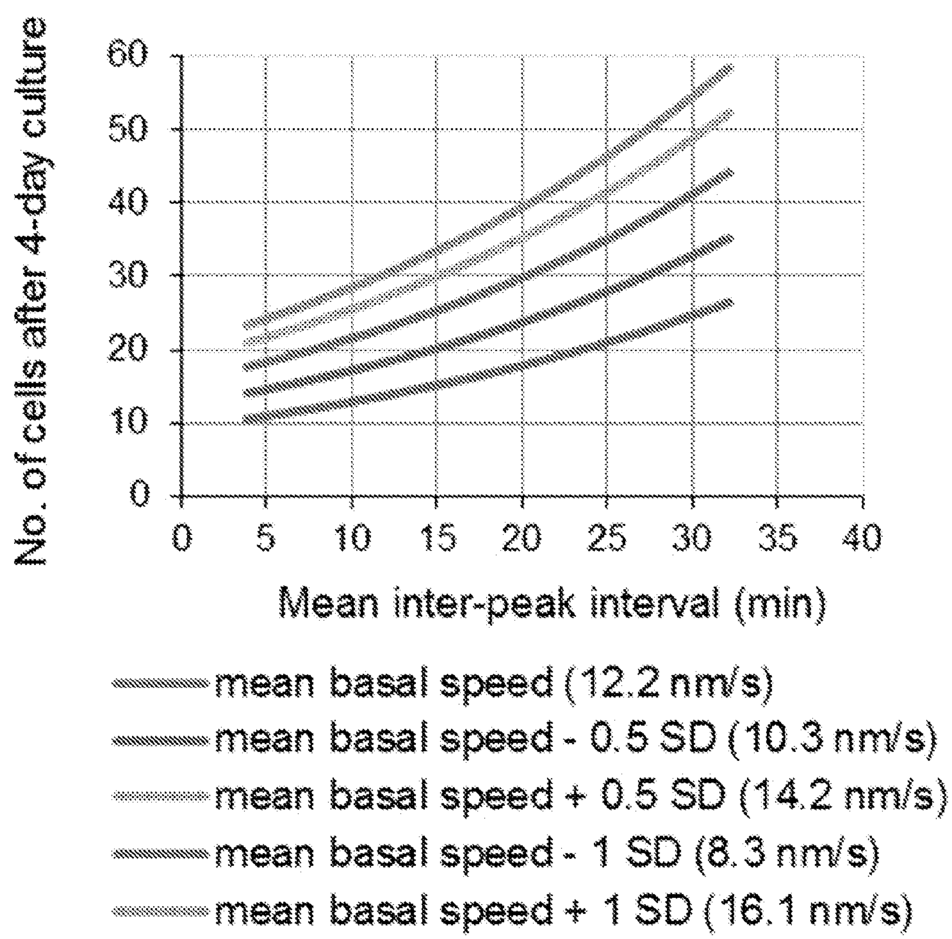
Figure 13A:
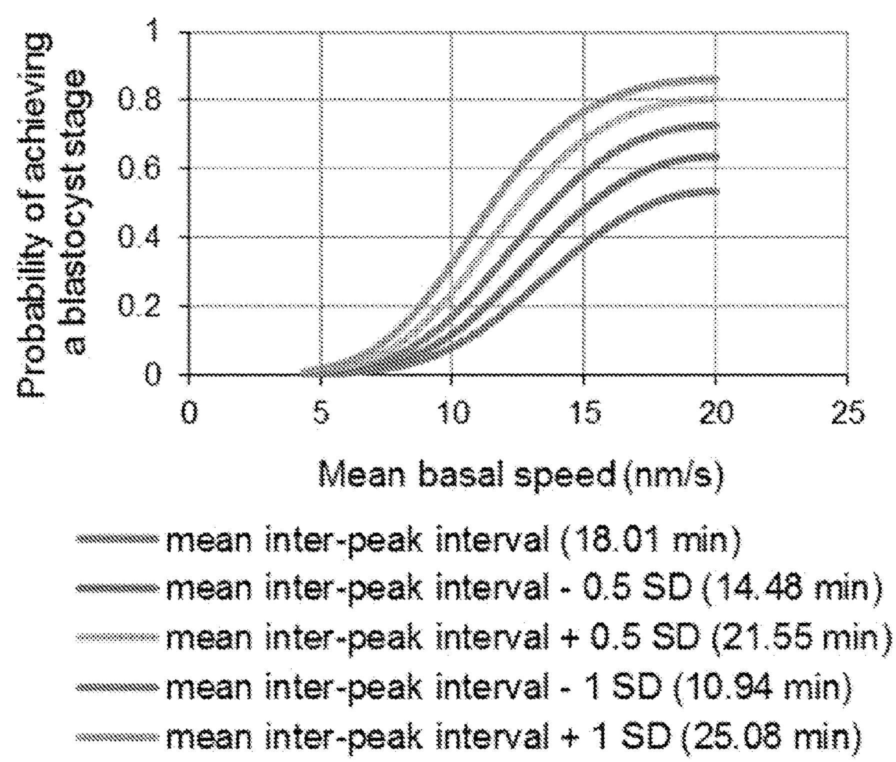
Figure 13B:
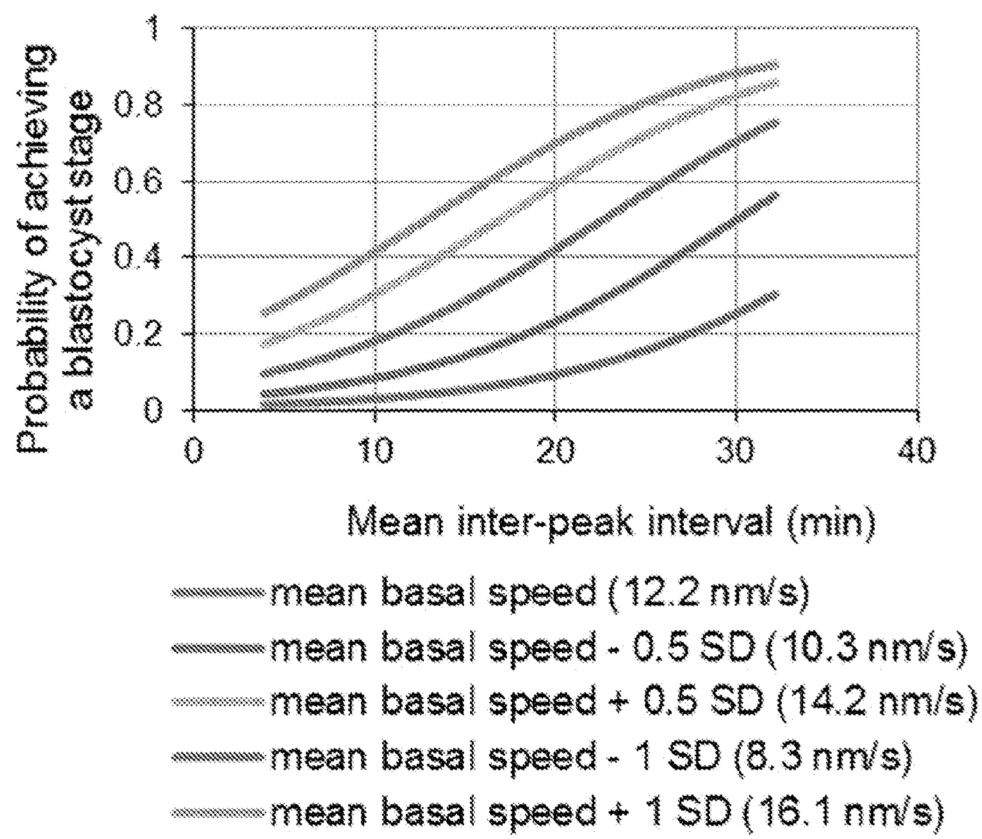

Since we found that cytoplasmic movements correspond to the pattern of $Ca^{2+}$ oscillations and the quality of the cytoskeleton, we wondered whether the analysis of such movements might be predictive of developmental success. To address this, we fertilized 71 eggs in vitro, recorded their cytoplasmic movements throughout the period that FCs were present and then cultured embryos for 4 days. In the first instance we related the pattern of cytoplasmic movements in each embryo with the total number of cells at this time. This revealed that for different values of the mean interval between speed-peaks there were statistically significant linear and quadratic effects between the mean basal speed (p=0.0005 and 0.0001 respectively) and the cell count in an embryo (in the log scale; FIG. 5C). The mean cell count at the $4^{th}$ day of development increased with the mean basal speed (up to 1.7 standard deviations (SD=6.7 nm/s) away from the average of 12.2 nm/s of the mean basal speed values) after which it flattened off or declined (FIG. 5A, C). Moreover, for different values of the mean basal speed or its square, the mean number of cells after 4 days of development increased in proportion to the mean interval between speed-peaks (1.3 times higher (95% CI: 1.07-1.47) for every 1 SD, i.e. approximately 7 min; p=0.0045, FIG. 5B, D). Similar findings were observed when we examined developmental success by assessing the probability of development to the blastocyst stage (FIG. 13A). This analysis suggests a linear relationship between the mean basal speed (p=0.009) and the logarithm of odds that the embryo achieves the blastocyst stage after 4 days of development: the probability of developing to a blastocyst increases as the mean basal speed increases. Moreover, we found that for every 1 SD increase in the mean interval between speed-peaks the odds of an embryo developing into a blastocyst increased 2.3-fold (95% CI: 1.10-4.89; p=0.027) (FIG. 13B).

Figure 13C:
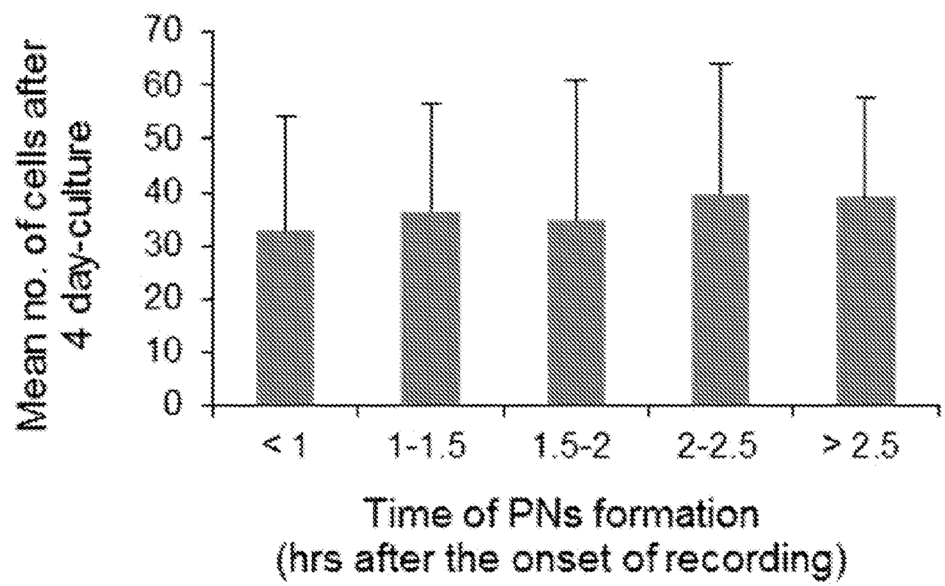
Figure 13D:
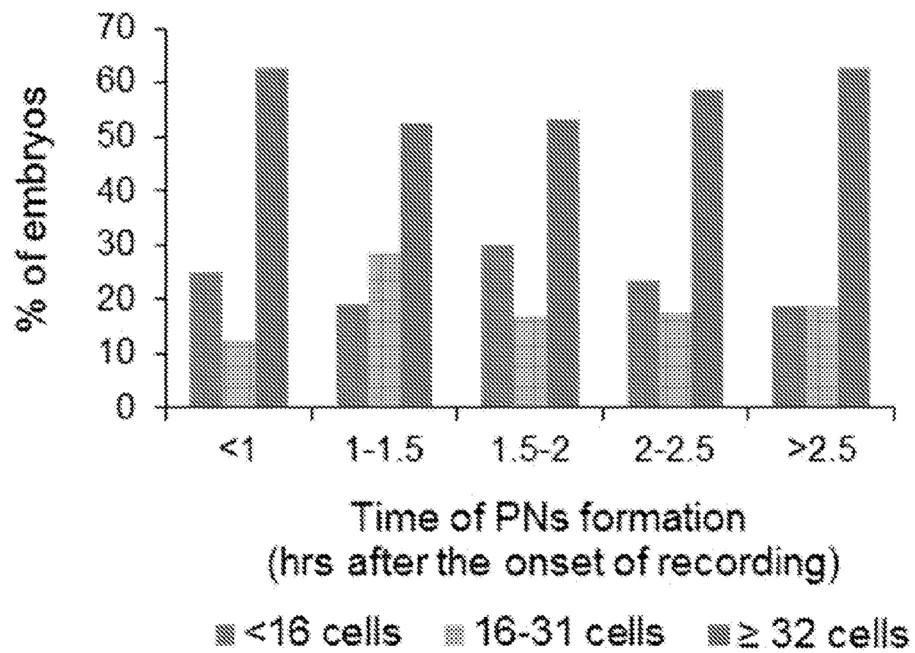
Figure 13E:
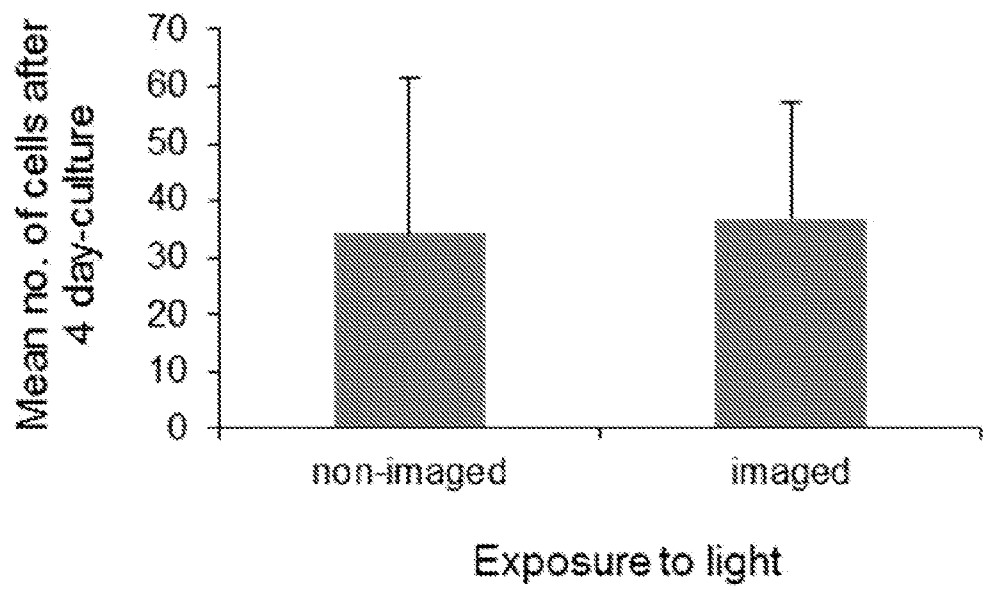
Figure 13F:
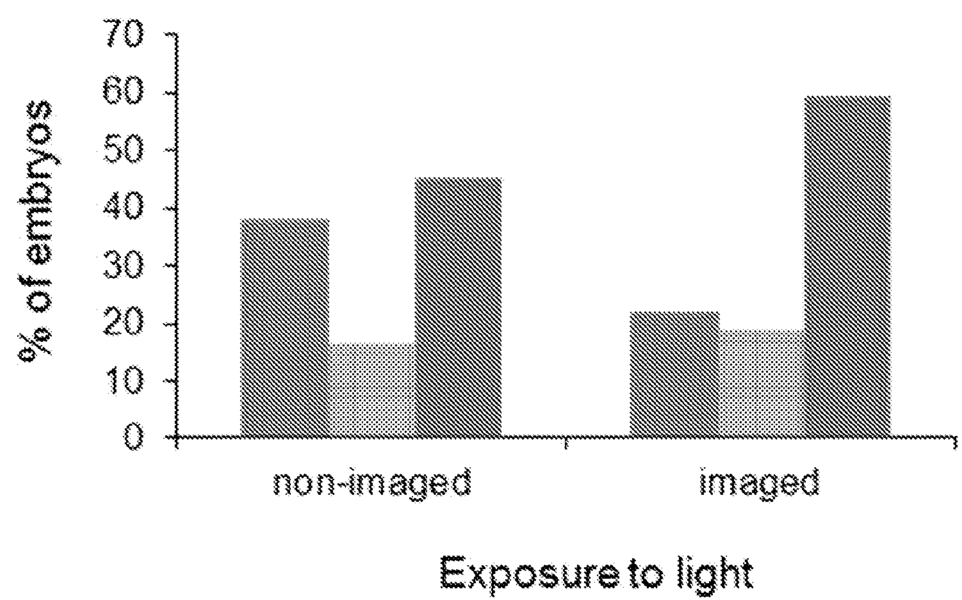

To eliminate the possibility that our method of recording cytoplasmic movements caused any photodamage and to examine whether any possible light sensitivity depended on the post-fertilization stage of imaging, we compared development of zygotes that formed pronuclei at different times after the onset of recording. We found no evidence of any differences either between the mean cell numbers or the distribution of developmental stages achieved (p>0.46 for any two compared groups and p=0.97, respectively, FIG. 13C, D). We also compared development of imaged (n=71) and non-imaged (n=46) embryos ensuring that both groups were treated in the same way. The mean number of cells (FIG. 13E) as well as the distribution of embryos with different cell numbers (FIG. 13F) were similar in both groups (p=0.75 and 0.19, respectively).

Figure 5E:
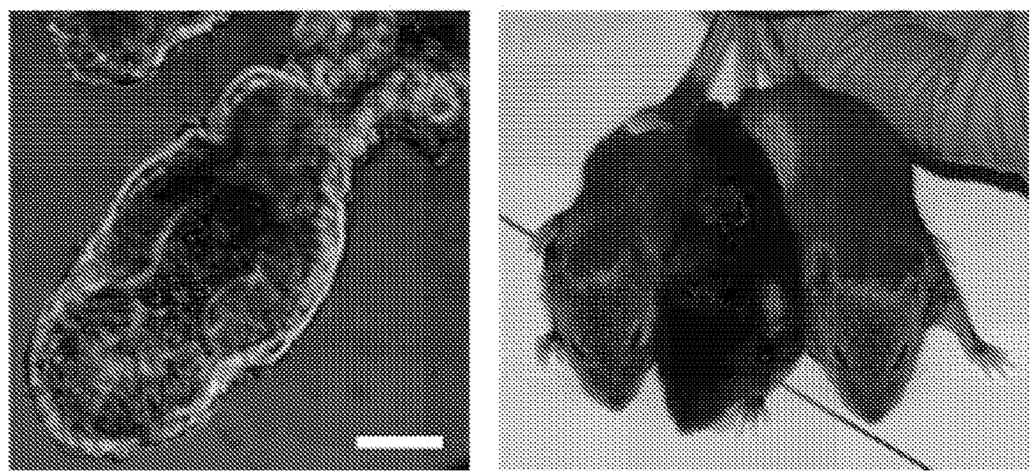
Figure 5F:
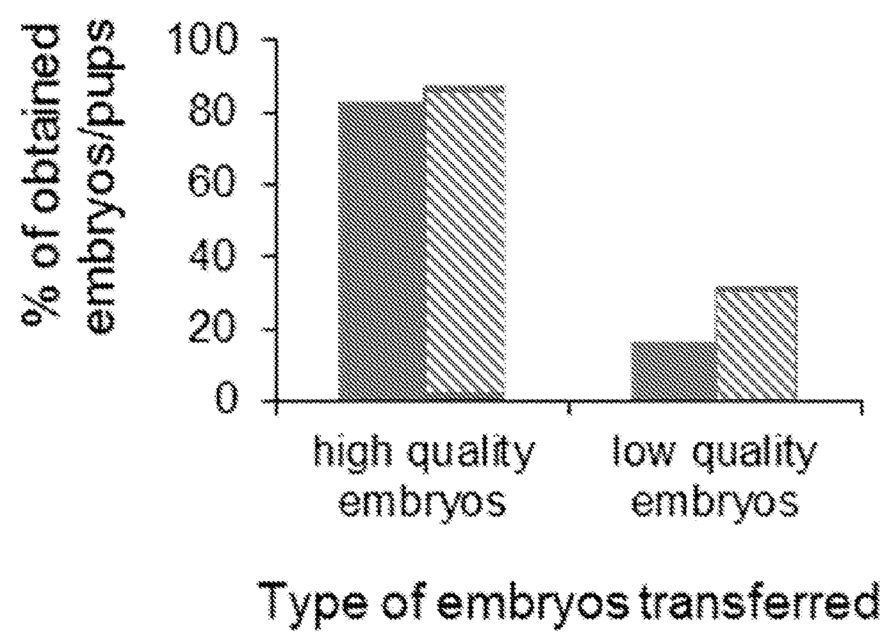

Finally, since the above results indicated that the pattern of cytoplasmic movements is predictive of pre-implantation development quality, we wished to determine whether these patterns of movements could predict which eggs would successfully develop to term. To this end, we imaged and analysed in vitro fertilized eggs and then grouped them accordingly to whether their cytoplasmic motion patterns would indicate good or poor developmental potential. Embryos with good potential were predicted to have after 4 days of culture between 25 and 52 (an average of 32) cells per embryo and to achieve the blastocyst stage in between 25 and 90% of cases (an average of 46.5%). Embryos classified as low quality would be predicted after 4 days to have between 9 and 24 cells (an average of 17) and that between 0 and 25% of them, an average of 10.7%, would achieve the blastocyst stage. The two groups of embryos were transferred at the 2-cell stage to the recipient females. Those embryos scored as 'high quality' developed to the egg cylinder stage (6.5 dpc) 5 times more often (83.3%, 5/6 vs. 16.7%, 1/6) and to full term (19.5 dpc) almost 3 times more often (2.77, 87.5%, 21/24 vs. 31.6%, 6/19) than embryos scored as 'low quality (FIG. 5E, F, Table 6). Taken together, these findings indicate that post-fertilisation cytoplasmic movements are predictive of developmental success and our method of imaging does not hinder embryo development.

Example 6

PLCζ-Induced $Ca^{2+}$ Oscillations Cause Coincident Cytoplasmic Movements in Human Oocytes Recent evidence suggests that the $Ca^{2+}$ oscillations at fertilization are triggered after the sperm fuses with the oocyte, and this leads to the introduction of a sperm-specific phospholipase C (PLCζ) into the oocyte[52,53]. PLCζ then generates repeated cycles of $InsP_3$ production within the ooplasm that cause the repetitive $Ca^{2+}$ release phenomenon of $Ca^{2+}$ oscillations[52, 53]. Sperm PLCζ is most conveniently introduced into oocytes by microinjection of its complementary RNA (cRNA) which is translated into PLCζ protein within the oocytes over a period of several hours[54]. Hence, the injection of PLCζ cRNA into oocytes produces the PLCζ protein that causes prolonged $Ca^{2+}$ oscillations, and in parallel experiments PLCζ has been shown to activate embryonic development of mouse, pig, cow and human oocytes up to the morula and blastocyst stages[54-57].

Here we report the use of PIV imaging in human oocytes that were injected with sperm PLCζ cRNA. We demonstrate that sudden but small cytoplasmic movements can be detected in near synchrony with each PLCζ induced $Ca^{2+}$ transient in human oocytes that had failed to fertilize after ICSI. The method we describe may have potential as a non-invasive method for monitoring $Ca^{2+}$ oscillation patterns in human oocytes.

Materials and Methods (Example 6)

Human Oocytes

Human oocytes were donated by patients in the IVF Wales clinic at the University Hospital of Wales, Cardiff. The current project and all associated procedures have been approved by the South East Wales Research Ethics Committee and the Human Fertilisation and Embryology Authority (R0161 held by K. Swann and N. Amso). Aged "failed ICSI" oocytes and fresh oocytes derived from follicle reduction procedures were used. ICSI was performed under standard conditions and the oocytes were cultured for a further 16-18 hours before they were judged to be fertilized or not. "Fresh oocytes" derived from follicle reduction and were used within 5 hours of collection. Only those oocytes that were ascertained as not activated were used in experiments. During the subsequent 1-4 hours these oocytes were transferred from the clinic to the research laboratory where they were microinjected with ~10-20 pl of human PLCζ cRNA, as described previously[54, 55]. Briefly cRNA was mixed with $Ca^{2+}$-sensitive dye, 0.5 mM Oregon Green BAPTA dextran, (OGBD, InVitrogen). This mixture was then microinjected using a micropipette (~1 μM tip diameter). The micropipette was inserted into the oocyte using a brief pulse of electrical oscillation from an amplifier that was connected in line to the micropipette needle. A pressure pulse (~1 second of 20 psi) was then applied to the back of the micropipette to push a bolus of the injection mixture into the oocyte. The cRNA was mixed with $Ca^{2+}$-sensitive dye, 0.5 mM Oregon Green BAPTA dextran, (OGBD, InVitrogen). PLCζ cRNA was prepared as described previously[54]. During the data collection, the oocytes were maintained at 37° C. in a drop of media under oil, using a Series 40 Quick Change imaging chamber with a CL-100 temperature controller (Warner Instruments). Oocytes were microinjected in M2 media (Sigma) and then recording was in HEPES buffered KSOM media, as described before[59].

Imaging System

The oocytes or zygotes were imaged for several hours after microinjection using a Nikon TiU epifluoroescence microscope with a 20×0.75 NA objective. Fluorescence excitation from a halogen lamp was passed through a 490 nm bandpass filter, reflected via a 505 nm dichroic, and collected with a 530 nm bandpass filter. White light from another halogen lamp was used to visualize the oocytes with differential interference phase contrast (DIC) microscopy. Shutters were placed in the path of these light sources, and filter wheels were in the path of both the fluorescence excitation and emission light such that oocytes were only briefly exposed to light during image acquisition. The shutters and filter wheels were controlled by a Lambda-10 controller (Sutter Instruments). Images were taken with 100-200 msec exposures in immediate succession every 10 seconds with a Coolsnap HQ2 CCD camera (Photometrics). The Lambda-10, image collection and initial analysis were controlled used InVivo software (Media Cybernetics) and images stored as tiff stacks.

The fluorescence images were analysed using ImageJ (http://rsbweb.nih.gov/ij/) and the fluorescence intensity of the dye from the whole oocyte was plotted against time. The movements in the cytoplasm were analyzed with cross-correlation methods that had been developed for studying similar movements in mouse zygotes[58]. The algorithm is based on that used in PIV analysis in fluid dynamics research and involves cross-correlating image sub-regions between successive pairs of images. This analysis gives a vector field representing the movement of local regions of cytoplasm. The mean speed of movement was calculated by taking the mean of the magnitude of the vectors in a square region in the centre of the oocyte, as described previously[58]. The software was developed and written in MATLAB and is available under an academic non-commercial use licence at http://users.ox.ac.uk/~zoo10847/code.html.

Results (Example 6)

Figure 6A:
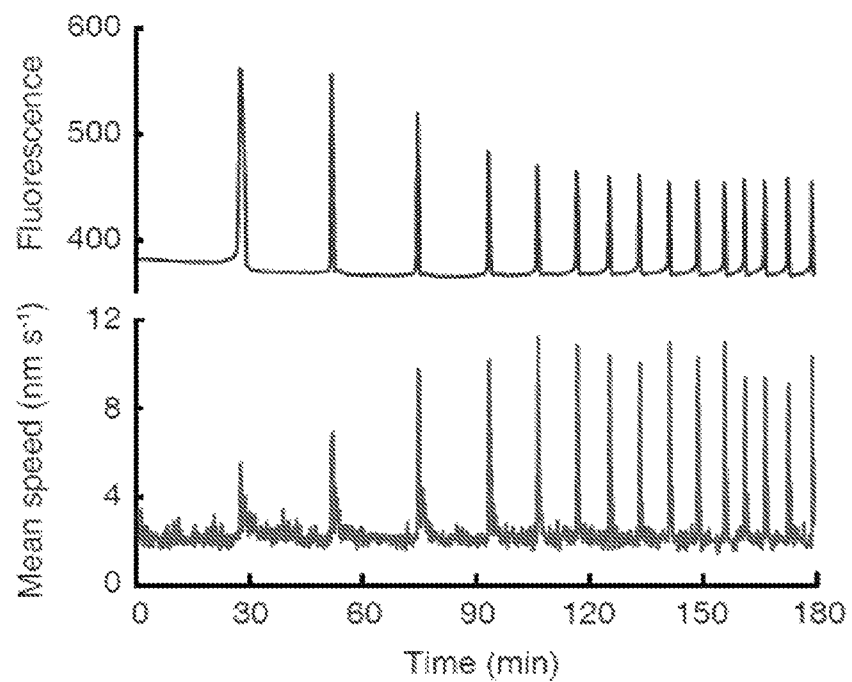

Microinjection of PLCζ cRNA into human oocytes that had failed to activate after ICSI caused a sustained series of $Ca^{2+}$ oscillations that are illustrated in FIG. 6A. The specific pattern of spikes of elevated free $Ca^{2+}$ showed some variation between oocytes, but the general response consisted of a large initial $Ca^{2+}$ increase, followed by a series of smaller $Ca^{2+}$ transients that gradually increased in frequency with time. This general pattern of $Ca^{2+}$ oscillations is similar to that reported previously in human oocytes that were injected with PLCζ cRNA[55]. The relatively long latency between cRNA injection (15-20 mins before the start of recording) and the first appearance of $Ca^{2+}$ spikes, and the subsequent build up in $Ca^{2+}$ spike frequency, probably reflects the gradual increase in expression of PLCζ protein with time that has previously been demonstrated empirically with luciferase-tagged fusion constructs of PLCζ[54, 60-62].

Figure 6B:
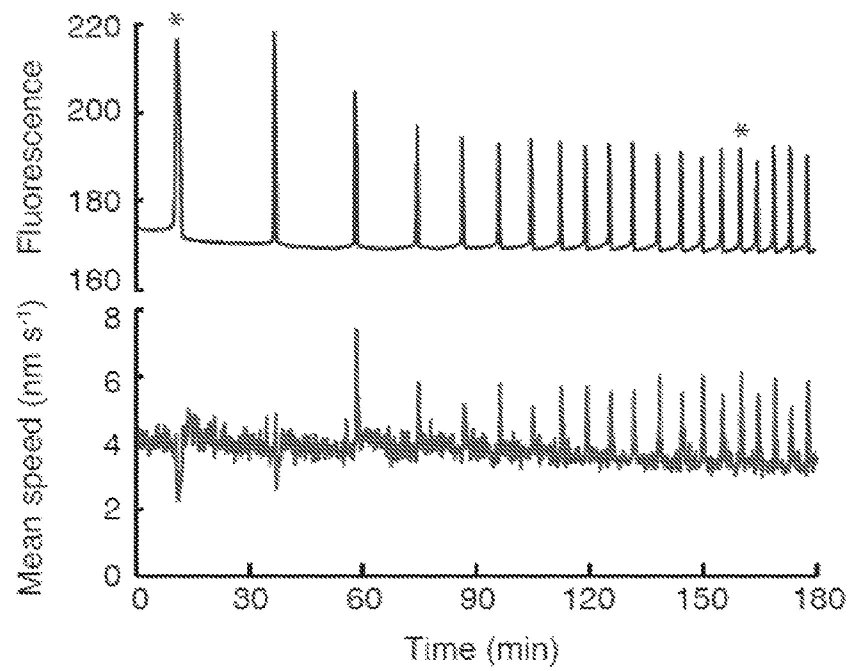
Figure 7:
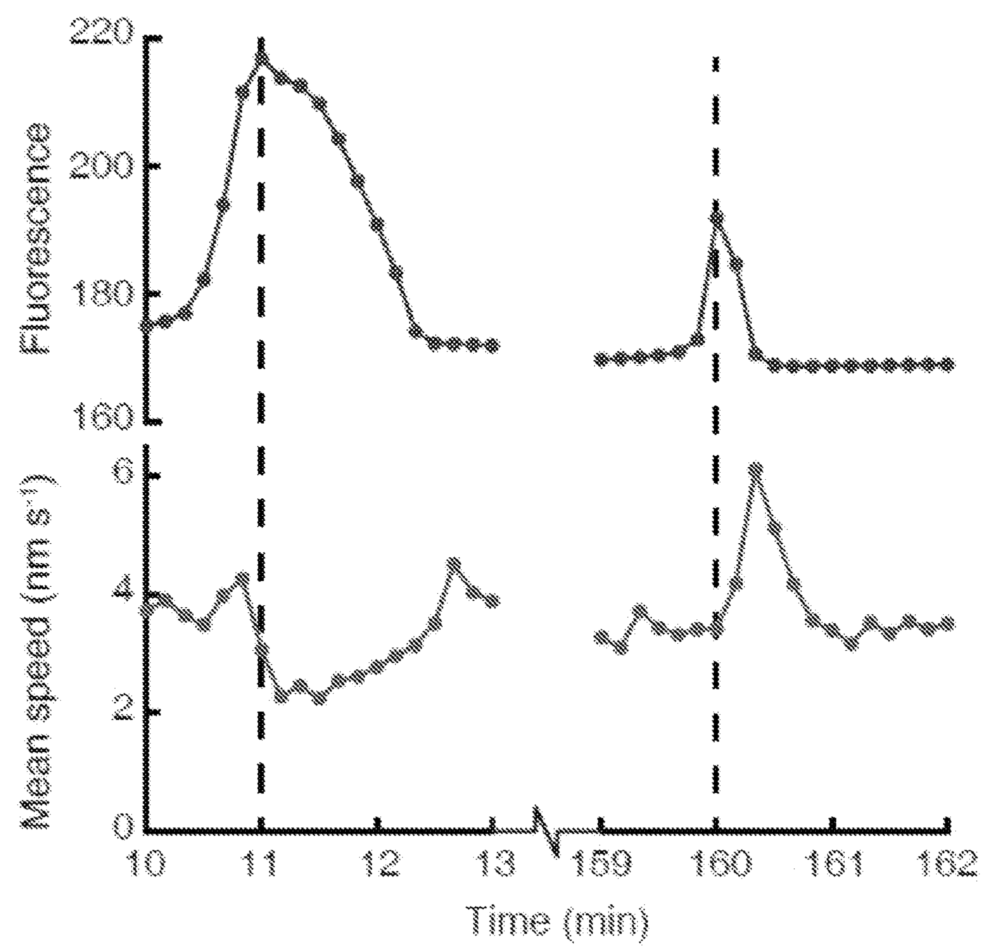

When we analysed the PLCζ cRNA-injected oocytes for cytoplasmic movements using PIV, we found that distinct movements occurred within the same 10 second interval, immediately after each $Ca^{2+}$ transient (FIG. 6B). In these human oocytes, the maximum mean PIV speed was either coincident with the maximum of the $Ca^{2+}$ spike, or it occurred within the 50 s following the maximum of the $Ca^{2+}$ transient. In total, 95/102 cytoplasmic movements were detected within this range from 10 different zygotes. The mean lag of the speed-peak was 18 seconds after the $Ca^{2+}$ peak (with a range 10-50 seconds). It is noteworthy that the movements detected in the oocyte cytoplasm are relatively small in scale: the mean magnitude of all vectors at a speed-peak never exceeded 40 nm/sec, and within these speed-peaks local regions never moved faster than 120 nm/sec. Even though in most cases there was a sudden increase in movement associated with a $Ca^{2+}$ transient, it was also notable that the higher level of $Ca^{2+}$ achieved in the first spike of some recordings was often accompanied by reduced movement in the cytoplasm (4/6 cases) (FIG. 6B). In one case, when the $Ca^{2+}$ level remained high at the second peak, the cytoplasmic movement was also suppressed (1/6) (FIGS. 6B and 7).

Figure 8:
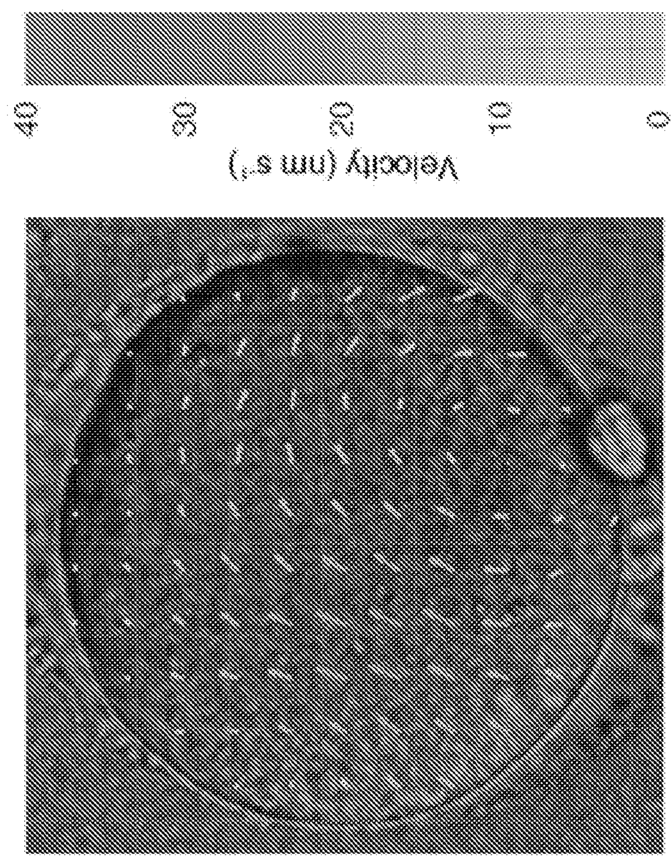
Figure 8:
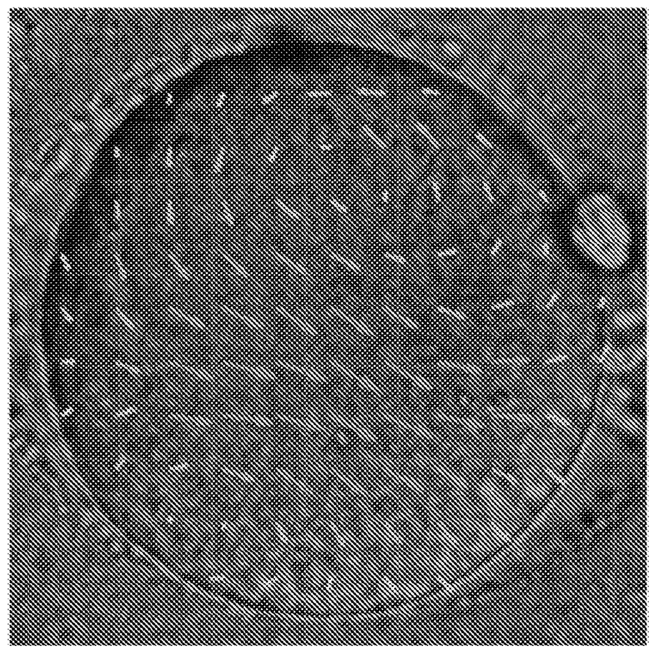
Figure 9B:
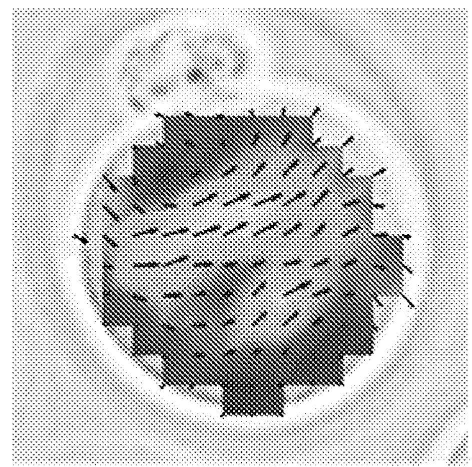
Figure 9A:
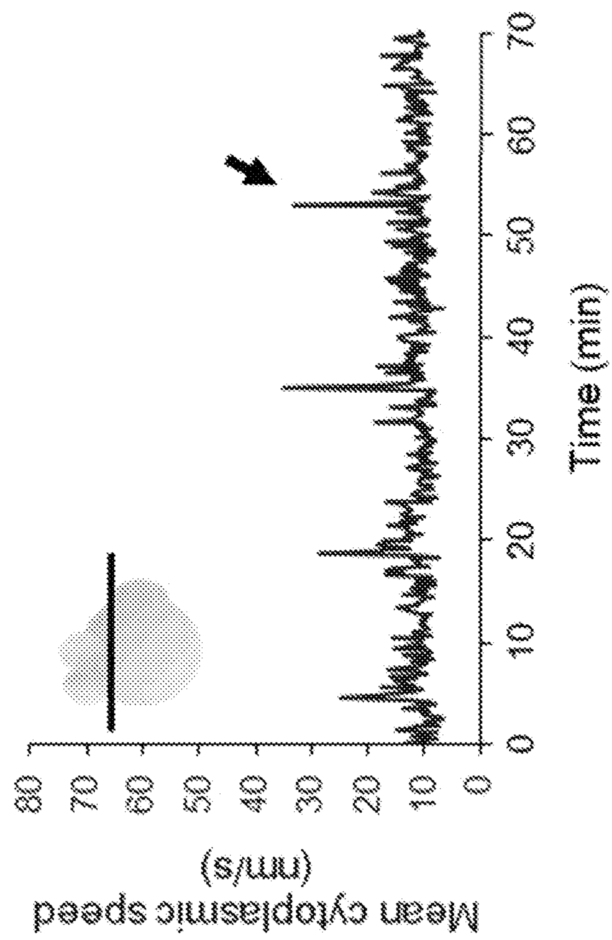
Figure 9D:
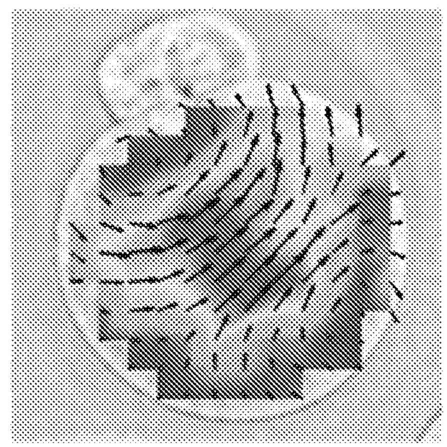
Figure 9C:
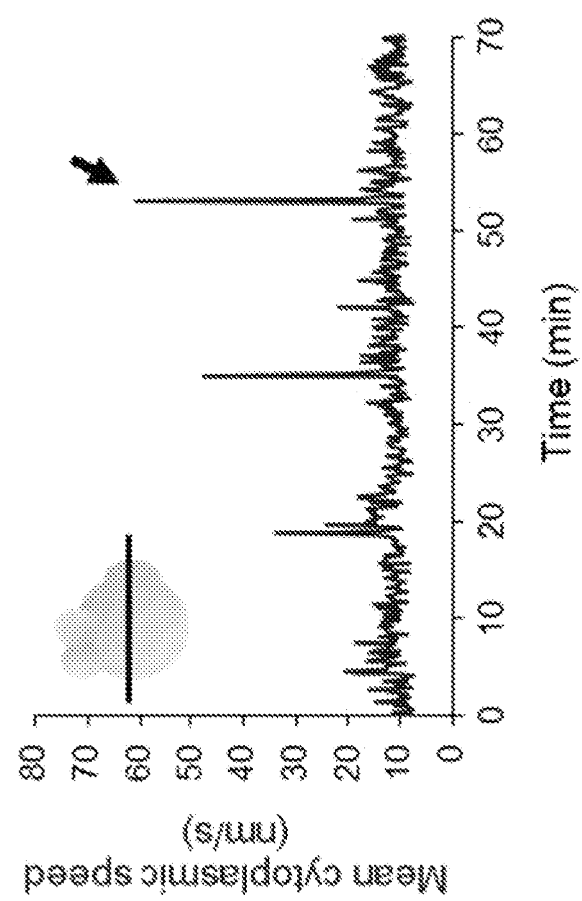
Figure 9F:
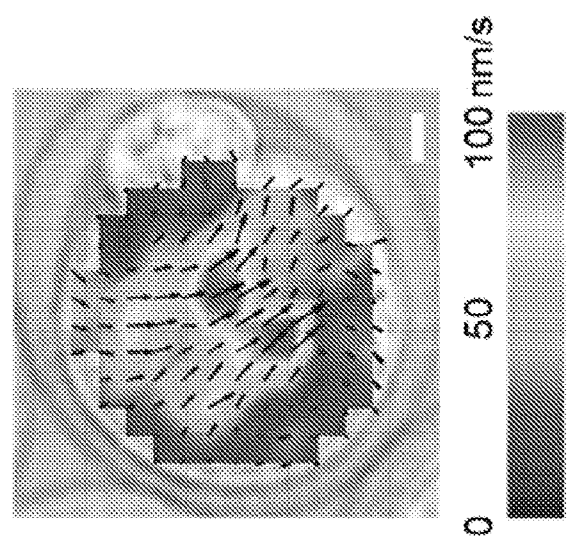
Figure 9E:
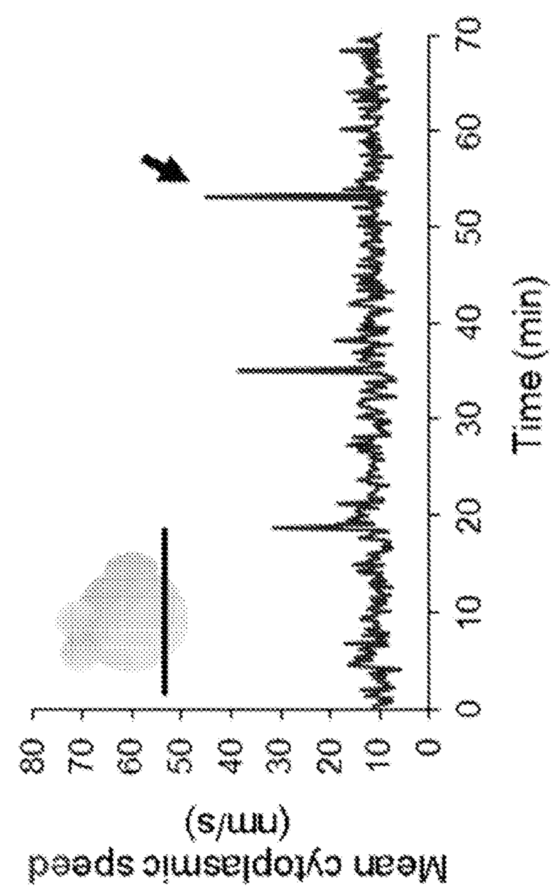
Figure 9G:
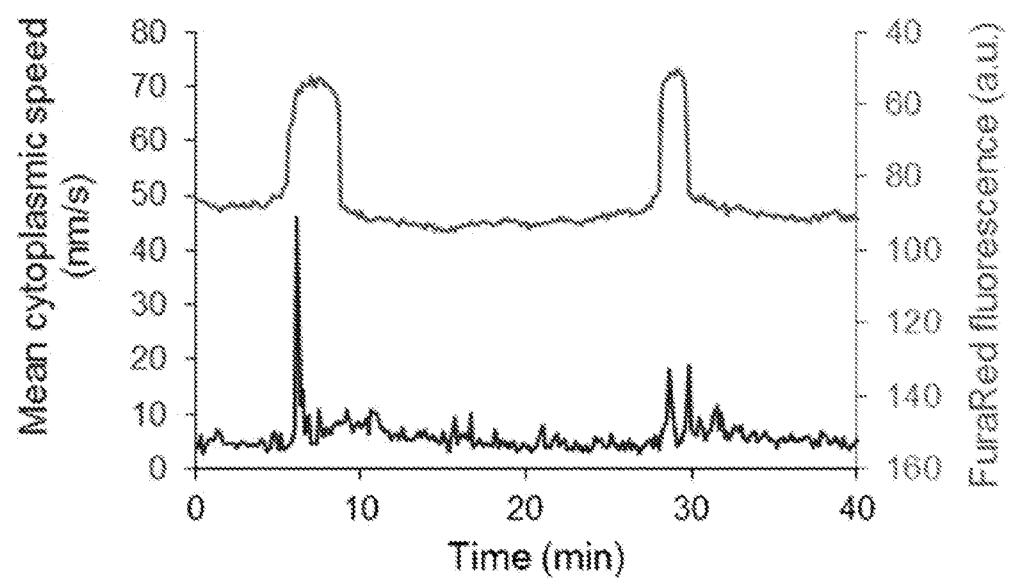

For individual oocytes, the vectors of movement had a consistent orientation during each speed-peak, but the direction of movement was often reversed within a spasm of movement (FIG. 8). However, the mean direction of movement had no consistent relationship with the position of the 1st or second polar bodies. In addition, small vortices were frequently visible in speed-peaks. Given the limitation of the small number of oocytes imaged in a single plane, these vortices were not obviously associated with any particular oocyte structure.

The degree of synchrony between $Ca^{2+}$ elevation and movement was the common finding in these human oocytes. This suggests that the cytoplasmic movements in human oocytes are directly induced by elevated free $Ca^{2+}$ ions. Previous studies in mouse zygotes showed that such movements in the cytoplasm are dependent upon the actin cytoskeleton and are greatly influenced by the presence of the sperm and fertilization cone[58]. It was difficult to identify the region of the activated human oocytes that changed shape during the speed-peaks, although there were slow progressive changes of cell profile detected during the recordings. In some records it was possible to observe a granular region moving around the cytoplasm and forming a thick granular crescent beneath the cell membrane. This peripheral crescent also moved in relation to the position of the 1st polar body but the precise crescent boundary was poorly defined. It remains unclear whether any potential sperm may be present within these "failed ICSI" oocytes or if any structures around a sperm could play a specific role in cytoplasmic movements, as suggested in mouse zygotes. However, we did carry out a similar analysis of PLCζ cRNA-induced $Ca^{2+}$ oscillations and cytoplasmic movements in 7 unfertilized oocytes that were obtained after follicle reduction. Notably, we failed to detect any movements associated with the 41 $Ca^{2+}$ spikes observed in these follicle reduction-derived oocytes.

Discussion

Non-invasive rapid time-lapse imaging combined with PIV analysis of cytoplasmic events after fertilization described here reveals that sperm entry into the mouse egg triggers a series of unexpected rhythmic actomyosin contractions associated with cytoplasmic movements. At their maximum speed these cytoplasmic movements have vectors directed towards the protrusion formed above the site of sperm entry that undergoes pulsations in synchrony with them. The speed-peaks of the cytoplasmic movements correspond in timing with fertilization induced $Ca^{2+}$ transients and they depend on calcium oscillations. We show that analysis of the interval between peaks provides a novel non-invasive and very rapid way of assessing the vitality of the embryo and its ability to succeed in development.

The involvement of the actomyosin cytoskeleton in mediating cytoplasmic movements is evident from our findings that inhibition of MLCK or treatments that either stabilised or depolymerised F-actin diminished both speed-peaks and the basal cytoplasmic speed. The movements also depend upon $Ca^{2+}$ transients because they were prevented by chelating $Ca^{2+}$ with BAPTA. One possibility is that $Ca^{2+}$-dependent kinases such as $Ca^{2+}$/calmodulin-dependent kinase II (CaMKII) or conventional protein kinase C (cPKC) participate in triggering the movements as these enzymes are known both to regulate the cytoskeleton[10] and respond to $Ca^{2+}$ oscillations[34-36]. However, whereas the amplitude of $Ca^{2+}$ oscillations are similar throughout the whole post-fertilization period (except for the first $Ca^{2+}$ spike that is usually bigger than subsequent ones[29]), the amplitude of the speed peaks increases at onset of FC formation and decreases upon FC regression. Moreover, the $Ca^{2+}$ transients evoked by parthenogenetic activation are not sufficient to promote fast, oscillatory cytoplasmic movements suggesting that additional fertilization-associated factors must enable the movements to take place.

The coincidence of robust speed-peaks of movement with actomyosin-mediated rhythmic movements of the FC suggests that these are manifestations of the same process. This is further borne out by studies of FC formation after sperm injection. As FC formation requires interaction of chromatin with cortical proteins[33], it does not occur when sperm is injected deep into the egg. Accordingly, eggs fertilized in this way showed much weaker speed-peaks than in zygotes with FCs. The fact that speed-peaks, although weak, were still present, could be because sperm chromatin was positioned close enough to the cell surface to cause some reorganization of the cortical actomyosin. Although insufficient to produce a well-defined FC, this would still be able to enhance weak cytoplasmic movements. Alternatively, the speed-peaks could be triggered by contractions of the cortical actomyosin accumulated above the maternally-derived chromatin. Indeed, we frequently could see that a bulge formed above the set of maternal chromosomes pulsates in a way similar to the FC. It is also possible that low amplitude speed-peaks may be an effect of general contractility of the actomyosin cytoskeleton, not associated with the cortex. The last two possibilities could also explain why there are some low-amplitude speed-peaks visible in the $Sr^{2+}$-activated parhenogenotes.

High speed movements were also not triggered and FC motions were very much diminished in $Sr^{2+}$-activated eggs injected with heat-inactivated sperm heads. Thus, the sperm may well contribute proteins that facilitate FC motions and cytoplasmic movements that are inactivated by heat treatment. It is also possible that differences observed between normal zygotes and embryos injected with inactivated sperm followed by $Sr^{2+}$ activation may be due to the altered characteristics of the $Ca^{2+}$ transients themselves. The dynamics of typical $Sr^{2+}$-induced $Ca^{2+}$ peaks differ from those of $Ca^{2+}$ peaks triggered by fertilization. Moreover, frequency of the $Sr^{2+}$-induced $Ca^{2+}$ oscillations was very high under our conditions and this seemed to affect negatively generation of high-amplitude speed-peaks.

We found that the timing and pattern of cytoplasmic movements provide a powerful indicator of embryo quality. Our data shows that embryos with low mean basal speed (below 10 nm/s; indicates poor quality of the actomyosin cytoskeleton), as well as embryos with very frequent speed-peaks (inter-peak interval below 10 min; reflecting frequent $Ca^{2+}$ transients), rarely develop to the blastocyst stage in vitro or to full term in vivo. This result accords with findings that both functional actin cytoskeleton and correct pattern of $Ca^{2+}$ transients (especially the total time of $Ca^{2+}$ elevation) are crucial for development[12, 15, 16, 37-39]. However, these factors cannot be used in research and medical facilities to select good quality embryos as they involve invasive procedures using fluorescent dyes and harmful irradiation. Thus, current practice in the in vitro fertilization clinic is to assess the viability of embryos on day 3 from their morphology and growth or at day 5, because of unreliability of the 3-day assessment[40-42]. A considerable advance may be offered by imaging and monitoring of a series of parameters over the first two days of development[43]. The vitality of the embryo and its ability to succeed in development may be assessed by using non-invasive imaging over a much shorter period of time, just 2 hours around the time of fertilization.

In conclusion, we have identified the importance of the sperm in triggering a dynamic oscillatory behavior of the actomyosin cytoskeleton at fertilization. The ensuing movements have a pattern and timing that provides a powerful method of assessing an egg's ability to achieve its full developmental potential. As such our method has considerable potential in finding practical application in the assisted reproduction clinic.

EQUIVALENTS

The foregoing written specification is considered to be sufficient to enable one skilled in the art to practice the invention. The present invention is not to be limited in scope by examples provided, since the examples are intended as a single illustration of one aspect of the invention and other functionally equivalent embodiments are within the scope of the invention. Various modifications of the invention in addition to those shown and described herein will become apparent to those skilled in the art from the foregoing description and fall within the scope of the appended claims. The advantages and objects of the invention are not necessarily encompassed by each embodiment of the invention.

All references, including patent documents, disclosed herein are incorporated by reference in their entirety for all purposes, particularly for the disclosure referenced herein.

TABLE 1

Mean amplitudes of speed peaks and after-movements in control and inhibitor-treated zygotes

| | | Mean amplitude of speed-peaks +/− s.d. (nm/s) | Mean amplitude of after-movements +/− s.d. (nm/s) |
|---|---|---|---|
| Control zygotes* | Stage 1‡ (18 zygotes, 45 peaks) | 29.7 +/− 19.4 | 8.7 +/− 2.8 |
| | Stage 2 (32 zygotes, 108 peaks) | 44.9 +/− 25.0 | 12.3 +/− 5.0 |
| | Stage 3 (55 zygotes, 88 peaks) | 12.2 +/− 10.0 | 17.7 +/− 6.4 |
| Nocodazole-treated zygotes | Stage 1 (3 zygotes, 7 peaks) | 20.6 +/− 11.2 | 11.1 +/− 3.9 |
| | Stage 2 (17 zygotes, 46 peaks) | 35.2 +/− 19.3§ | 16.6 +/− 6.8¶ |
| | Stage 3 (66 zygotes, 115 peaks) | 10.4 +/− 8.5 | 21.5 +/− 6.7‖ |
| Taxol-treated zygotes | Stage 1 (3 zygotes, 6 peaks) | 18.0 +/− 5.0¶ | 7.9 +/− 4.3 |
| | Stage 2 (15 zygotes, 37 peaks) | 29.9 +/− 21.0¶ | 11.1 +/− 5.3 |
| | Stage 3 (18 zygotes, 33 peaks) | 11.5 +/− 6.5 | 14.3 +/− 5.8¶ |
| Jasplakinolide-treated zygotes | Stage 1† (1 zygote, 3 peaks) | 20.9 +/− 10.1 | 5.2 +/− 2.1 |
| | Stage 2 (22 zygotes, 50 peaks) | 14.5 +/− 8.3‖ | 4.2 +/− 1.9‖ |
| | Stage 3 (57 zygotes, 102 peaks) | 10.8 +/− 7.6 | 3.8 +/− 2.8‖ |

*Mean amplitudes of speed peaks and after-movements differ significantly between analyzed stages.

‡Post-fertilization stages are described in the main text.

†Statistics was not applied to values from Stage 1 of jasplakinolide-treated zygotes due to the low number of these peaks/embryos.

§$p < 0.05$ vs control,

¶$p < 0.01$ vs control,

‖$p < 0.0001$ vs control

TABLE 2

Influence of $Ca^{2+}$ chelation and cytoskeleton inhibitors and on basal cytoplasmic speed in fertilized mouse eggs

| | Control zygotes (n = 82) | Unfertilized eggs (n = 55) | BAPTA-treated zygotes (n = 20) | Nocodazole-treated zygotes (n = 38) | Taxol-treated zygotes (n = 27) | Cytochalasin D-treated zygotes (n = 21) | Jasplakinolide-treated zygotes (n = 60) | ML-7-treated zygotes (n = 17) |
|---|---|---|---|---|---|---|---|---|
| Mean basal cytoplasmic speed +/− s.d. (nm/s) | 9.0 +/− 1.9 | 4.3 +/− 1.0* | 15.3 +/− 3.3* | 11.0 +/− 1.5* | 7.7 +/− 1.7[§] | 3.1 +/− 0.6* | 3.0 +/− 0.4* | A. 5.1 +/− 1.3[*,‡]<br>B. 8.3 +/− 1.1[†,‡] |

A - mean basal velocity before M-phase/interphase transition
B - mean basal velocity after M-phase/interphase transition
*p < 0.000 1 vs. control zygotes,
[§]p < 0.001 vs. control zygotes,
[†]p < 0.05 vs. control zygotes,
[‡] p < 0.000 1 between marked values

TABLE 3

Mean amplitudes of speed peaks and after-movements in embryos obtained by ICSI or by activation with $SrCl_2$

| Embryos obtained by: | Post-fertilization stages | Mean amplitude of speed-peaks +/− s.d. (nm/s) | Mean amplitude of after-movements +/− s.d. (nm/s) |
|---|---|---|---|
| ICSI under the cortex | Stage 1* (6 zygotes, 9 peaks) | 19.5 +/− 11.1 | 10.7 +/− 5.9 |
| | Stage 2 (14 zygotes, 66 peaks) | 34.1 +/− 15.4 | 12.8 +/− 5.0 |
| | Stage 1 prolonged[‡] (14 zygotes, 75 peaks) | 32.3 +/− 15.7 | 12.5 +/− 5.1 |
| | Stage 3 (16 zygotes, 28 peaks) | 14.3 +/− 9.4 | 13.6 +/− 4.9 |
| ICSI into the central cytopalsm | Stage 1 prolonged[‡] (31 zygotes, 209 peaks) | 14.6 +/− 8.2[#] | 10.5 +/− 14.7 |
| | Stage 3 (31 zygotes, 37 peaks) | 10.3 +/− 6.8 | 12.4 +/− 3.5 |
| Activation with $SrCl_2$[§] | Stage 1 prolonged[‡] (45 parthenotes, 337 peaks[†]) | 7.4 +/− 4.0[#,‖,¶] | 7.7 +/− 2.9[#,**] |
| ICSI with the inactivated sperm and $SrCl_2$ activation | Stage1 (10 zygotes, 30 peaks) | 8.8 +/− 8.8[‖] | 7.9 +/− 3.0 |
| | Stage 2 (16 zygotes, 71 peaks) | 8.6 +/− 5.4[#] | 10.1 +/− 3.5[#,‡‡] |
| | Stage 3 (19 zygotes, 71 peaks) | 7.1 +/− 4.3[#] | 13.0 +/− 7.0 |

*Post-fertilization stages are described in the main text.
[‡]Stage 2 (i.e. fully formed FC) was not present in eggs injected with sperm into the central cytoplasm or eggs activated with $SrCl_2$, thus name 'Stage 1 prolonged' refers to the period between onset of 2PB formation and formation of pronuclei.
[†]In case of $SrCl_2$-activated eggs, a total number of speed-peaks and, if speed-peaks were absent, after-movements is shown.
[§]Speed-peaks and after-movements ceased in $SrCl_2$-activated eggs before pronuclei became visible, thus Stage 3 is not analysed.
[#]p < 0.001 vs an analogous stage in zygotes obtained by ICSI under the cortex;
[‖]p < 0.05 vs Stage 1 in zygotes obtained by ICSI under the cortex;
[¶]p < 0.000 1 vs zygotes obtained by ICSI into the central cytoplasm;
**p < 0.01 vs zygotes obtained by ICSI into the central cytoplasm;
[‡‡]p < 0.001 vs prolonged Stage 1 in $SrCl_2$-activated eggs

TABLE 4

Direction of vectors during speed-peaks at different post-fertilization stages

| Post-fertilization stages[†] | Total no. of analysed speed peaks | No. of speed peaks with vectors pointing in a specified direction* (%): Towards 2PB | Between 2PB and FC | Towards FC | No predominant direction |
|---|---|---|---|---|---|
| Stage 1 (11 zygotes) | 25 | 17[‡] (66.7) | 6 (25.9) | 2[§] (7.4) | 0 |

TABLE 4-continued

Direction of vectors during speed-peaks at different post-fertilization stages

| Post-fertilization stages[†] | Total no. of analysed speed peaks | No. of speed peaks with vectors pointing in a specified direction* (%): Towards 2PB | Between 2PB and FC | Towards FC | No predominant direction |
|---|---|---|---|---|---|
| Stage 2 (19 zygotes) | 65 | 1[‡] (1.5) | 22 (33.8) | 42[§] (64.6) | 0 |

TABLE 4-continued

| Direction of vectors during speed-peaks at different post-fertilization stages | | | | | |
|---|---|---|---|---|---|
| | Total no. | No. of speed peaks with vectors pointing in a specified direction* (%): | | | |
| Post-fertilization stages† | of analysed speed peaks | Towards 2PB | Between 2PB and FC | Towards FC | No pre-dominant direction |
| Stage 3 (19 zygotes) | 34 | 7 (20.6) | 4 (11.8) | 8 (23.5) | 15 (44.1) |

*The direction of movement was judged as described in the Materials and Methods.

†Stages of the zygote development are described in the main text.

‡,§ $p < 0.0001$

TABLE 5

Influence of $Ca^{2+}$ chelation and cytoskeleton inhibitors on completion of meiosis in in vivo fertilized mouse eggs

| | Total no. of zygotes* | Zygotes that failed to extrude 2PB (%) | Zygotes that extruded 2PB (%) |
|---|---|---|---|
| Control zygotes | 52 | 0 | 52 (100) |
| BAPTA-treated zygotes | 6 | 2 (33.3) | 4 (66.7) |
| Nocodazole-treated zygotes | 12 | 7 (58.3) | 5 (41.7) |
| Taxol-treated zygotes | 12 | 12 (100) | 0 |
| Cytochalasin D-treated zygotes | 10 | 10 (100) | 0 |
| Jasplakinolide-treated zygotes | 23 | 23 (100) | 0 |
| ML-7-treated zygotes | 13 | 4 (30.8) | 9 (69.2) |

*Only zygotes that did not extrude 2PB before the onset of recording were included to this analysis.

TABLE 6

Comparison between predicted quality and actual developmental potential of the embryos

| No. 1 | No. of embryos transferred 2 | Mean basal speed (nm/s) 3 | Mean interval between speed-peaks (min) 4 | Predicted no. of cells after 4-day culture (mean +/− s.d.) 5 | Predicted probability of achieving blastocyst stage after 4-day culture (%) (mean +/− s.d.) 6 | Estimated likehood of developmental success (high or low) 7 | Time of dissection (dpc) 8 | No. of embryos/pups 9 | No. of resorptions 10 | Efficiency of the transfer (%) 11 |
|---|---|---|---|---|---|---|---|---|---|---|
| 1 | 6 | 11.2 | 21.4 | 28 | 35-40 | high | 6.5 | 5 | — | 83.3 |
| | | 12.3 | 19.1 | 29 | 40 | | | | | |
| | | 11.1 | 25.9 | 32 | 45-50 | | | | | |
| | | 13.2 | 20.1 | 33 | 50-55 | | | | | |
| | | 16.0 | 20.3 | 39-40 | 65-70 | | | | | |
| | | 14.1 | 33.2 | 52 | 85-90 | | | | | |
| | | | | (36 +/− 9) | (56 +/− 19) | | | | | |
| 2 | 6 | 6.7 | 9.4 | 9-10 | 0.5 | low | 6.5 | 1 | — | 16.7 |
| | | 8.6 | 13.6 | 15-16 | 5-10 | | | | | |
| | | 10.5 | 9.2 | 17 | 5-10 | | | | | |
| | | 10.4 | 13.1 | 19 | 10-15 | | | | | |
| | | 11.2 | 9.7 | 19 | 10-15 | | | | | |
| | | 9.4 | 23.2 | 23-24 | 20-25 | | | | | |
| | | | | (17 +/− 5) | (11 +/− 7) | | | | | |
| 3 | 5 | 12.5 | 15.3 | 25-26 | 30-35 | high | 19.5 | 4 | —* | 80 |
| | | 11.4 | 18.7 | 26 | 30-35 | | | | | |
| | | 14.0 | 13.1 | 27-28 | 35-40 | | | | | |
| | | 13.5 | 16.1 | 29-30 | 40-45 | | | | | |
| | | 13.5 | 18.1 | 31-32 | 45-50 | | | | | |
| | | | | (28 +/− 3) | (39 +/− 7) | | | | | |
| 4 | 9 | 11.2 | 18.8 | 25-26 | 25-30 | high | 19.5 | 7 | —* | 77.8 |
| | | 11.4 | 17.8 | 25-26 | 25-30 | | | | | |
| | | 9.8 | 24.6 | 26-27 | 30-35 | | | | | |
| | | 12.8 | 16.7 | 28-29 | 35-40 | | | | | |
| | | 13.9 | 17 | 31 | 45-50 | | | | | |
| | | 13.8 | 17.9 | 32 | 50 | | | | | |
| | | 14.7 | 17.3 | 33-34 | 50-55 | | | | | |
| | | 16.2 | 17.2 | 36 | 60-65 | | | | | |
| | | 16.8 | 19.1 | 38-39 | 65-70 | | | | | |
| | | | | (31 +/− 5) | (45 +/− 15) | | | | | |
| 5 | 5 | 18.2 | 14.6 | 35-40 | 60-70 | high | 19.5 | 5 | —* | 100 |
| | | 17.2 | 17.6 | 38 | 65-70 | | | | | |
| | | 15.6 | 20.0 | 38-39 | 65-70 | | | | | |
| | | 16.2 | 20.7 | 40-41 | 70-75 | | | | | |
| | | 15.9 | 29.7 | 53-54 | 80-90 | | | | | |
| | | | | (42 +/− 7) | (72 +/− 8) | | | | | |
| 6 | 5 | 12.3 | 20.5 | 30-31 | 40-45 | high | 19.5 | 5 | —* | 100 |
| | | 12.7 | 21.9 | 33 | 50 | | | | | |
| | | 13.7 | 19.7 | 33-34 | 50-55 | | | | | |
| | | 12.4 | 24.8 | 35-36 | 55-60 | | | | | |

TABLE 6-continued

Comparison between predicted quality and actual developmental potential of the embryos

| No. 1 | No. of embryos transferred 2 | Mean basal speed (nm/s) 3 | Mean interval between speed-peaks (min) 4 | Predicted no. of cells after 4-day culture (mean +/− s.d.) 5 | Predicted probability of achieving blastocyst stage after 4-day culture (%) (mean +/− s.d.) 6 | Estimated likehood of developmental success (high or low) 7 | Time of dissection (dpc) 8 | No. of embryos/pups 9 | No. of resorptions 10 | Efficiency of the transfer (%) 11 |
|---|---|---|---|---|---|---|---|---|---|---|
| | | 12.8 | 23.7 | 36-37 | 55-60 | | | | | |
| | | | | (34 +/− 2) | (52 +/− 6) | | | | | |
| 7 | 5 | 10.0 | 5.5 | 10-15 | 5 | low | 19.5 | 3 | 0 | 60 |
| | | 11.3 | 7.4 | 18 | 10 | | | | | |
| | | 10.4 | 11.5 | 18 | 10 | | | | | |
| | | 10.2 | 16.8 | 21-22 | 15-20 | | | | | |
| | | 10.5 | 18.3 | 22-23 | 20 | | | | | |
| | | | | (19 +/− 4) | (13 +/− 6) | | | | | |
| 8 | 6 | 8.1 | 6.4 | 11-12 | 0-5 | low | 19.5 | 1 | 2 | 16.7 |
| | | 9.4 | 6.4 | 13-14 | 0-5 | | | | | |
| | | 9.2 | 17.1 | 18-19 | 10-15 | | | | | |
| | | 10.1 | 16.4 | 20-21 | 15-20 | | | | | |
| | | 10.2 | 16.0 | 20-21 | 15-20 | | | | | |
| | | 13.3 | 7.4 | 21-22 | 20 | | | | | |
| | | | | (18 +/− 4) | (12 +/− 8) | | | | | |
| 9 | 4 | 9.5 | 7.3 | 10 | 0-5 | low | 19.5 | 1* | 1 | 25 |
| | | 9.2 | 9.7 | 14-15 | 0-5 | | | | | |
| | | 9.8 | 13.3 | 14-15 | 5-10 | | | | | |
| | | 7.2 | 8.0 | 18-19 | 10-15 | | | | | |
| | | | | (14 +/− 3) | (6 +/− 5) | | | | | |
| 10 | 4 | 6.6 | 6.7 | 13-14 | 0-5 | low | 19.5 | 1* | 3 | 25 |
| | | 10.1 | 5.5 | 14-15 | 0-5 | | | | | |
| | | 13.5 | 4.4 | 19-20 | 10-20 | | | | | |
| | | 12.1 | 10.1 | 20-22 | 15-20 | | | | | |
| | | | | (17 +/− 4) | (9 +/− 8) | | | | | |

*Delivered naturally on 19.5 dpc.
*Found dead after 2 days.

TABLE 7

Optical specifications of the imaging systems used in experiments

| | Zeiss LSM 510 Meta | Zeiss Axiovert | Deltavision |
|---|---|---|---|
| Objective magnification | 20x* | 20x | 20x |
| Objective NA | 0.75 | 0.75 | 0.75 |
| Condenser NA | 0.55 | 0.55 | 0.55 |
| Chip size of the camera (pixels) | —# | 1024 × 1344 | 512 × 512 |
| Binning | — | 2 × 2 | 1 × 1 |

*The area of the scan was increased digitally prior to scan 0.7x (final magnification 14x)
Images were scanned with 1800 × 1800 pixel resolution.

REFERENCES

1. Roegiers, F., McDougall, A. & Sardet, C. The sperm entry point defines the orientation of the calcium-induced contraction wave that directs the first phase of cytoplasmic reorganization in the ascidian egg. *Development* 121, 3457-3466 (1995).
2. Sardet, C., Paix, A., Prodon, F., Dru, P. & Chenevert, J. From oocyte to 16-cell stage: cytoplasmic and cortical reorganizations that pattern the ascidian embryo. *Dev Dyn* 236, 1716-1731 (2007).
3. Speksnijder, J. E., Sardet, C. & Jaffe, L. F. The activation wave of calcium in the ascidian egg and its role in ooplasmic segregation. *J Cell Biol* 110, 1589-1598 (1990).
4. Stack, C., Lucero, A. J. & Shuster, C. B. Calcium-responsive contractility during fertilization in sea urchin eggs. *Dev Dyn* 235, 1042-1052 (2006).
5. Weaver, C. & Kimelman, D. Move it or lose it: axis specification in *Xenopus*. *Development* 131, 3491-3499 (2004).
6. Gerhart, J. et al. Cortical rotation of the *Xenopus* egg: consequences for the anteroposterior pattern of embryonic dorsal development. *Development* 107 Suppl, 37-51 (1989).
7. Abbott, A. L. & Ducibella, T. Calcium and the control of mammalian cortical granule exocytosis. *Front Biosci* 6, D792-806 (2001).
8. FitzHarris, G., Marangos, P. & Carroll, J. Cell cycle-dependent regulation of structure of endoplasmic reticulum and inositol 1,4,5-trisphosphate-induced Ca2+ release in mouse oocytes and embryos. *Mol Biol Cell* 14, 288-301 (2003).
9. Sun, Q. Y. et al. Translocation of active mitochondria during pig oocyte maturation, fertilization and early embryo development in vitro. *Reproduction* 122, 155-163 (2001).
10. Ducibella, T. & Fissore, R. The roles of Ca2+, downstream protein kinases, and oscillatory signaling in regulating fertilization and the activation of development. *Dev Biol* 315, 257-279 (2008).
11. Tombes, R. M., Simerly, C., Borisy, G. G. & Schatten, G. Meiosis, egg activation, and nuclear envelope breakdown are differentially reliant on Ca2+, whereas germinal vesicle breakdown is Ca2+ independent in the mouse oocyte. *J Cell Biol* 117, 799-811 (1992).
12. Toth, S., Huneau, D., Banrezes, B. & Ozil, J. P. Egg activation is the result of calcium signal summation in the mouse. *Reproduction* 131, 27-34 (2006).
13. Ozil, J. P. et al. Egg activation events are regulated by the duration of a sustained [Ca2+] cyt signal in the mouse. *Dev Biol* 282, 39-54 (2005).

14. Ducibella, T. et al. Egg-to-embryo transition is driven by differential responses to Ca(2+) oscillation number. *Dev Biol* 250, 280-291 (2002).

15. Ozil, J. P., Banrezes, B., Toth, S., Pan, H. & Schultz, R. M. Ca2+ oscillatory pattern in fertilized mouse eggs affects gene expression and development to term. *Dev Biol* 300, 534-544 (2006).

16. Ozil, J. P. & Huneau, D. Activation of rabbit oocytes: the impact of the Ca2+ signal regime on development. *Development* 128, 917-928 (2001).

17. Maro, B., Johnson, M. H., Pickering, S. J. & Flach, G. Changes in actin distribution during fertilization of the mouse egg. *J Embryol Exp Morphol* 81, 211-237 (1984).

18. Maro, B., Johnson, M. H., Webb, M. & Flach, G. Mechanism of polar body formation in the mouse oocyte: an interaction between the chromosomes, the cytoskeleton and the plasma membrane. *J Embryol Exp Morphol* 92, 11-32 (1986).

19. Gray, D. et al. First cleavage of the mouse embryo responds to change in egg shape at fertilization. *Curr Biol* 14, 397-405 (2004).

20. Deguchi, R., Shirakawa, H., Oda, S., Mohri, T. & Miyazaki, S. Spatiotemporal analysis of Ca(2+) waves in relation to the sperm entry site and animal-vegetal axis during Ca(2+) oscillations in fertilized mouse eggs. *Dev Biol* 218, 299-313 (2000).

21. Raffel, M., Willert, C. E. & Kompenhans, J. (Springer, 1998).

22. Willert, C. E. & Gharib, M. Digital particle image velocimetry. *Exp Fluids* 10, 181-193 (1991).

23. Keane, R. D. & Adrian, R. J. Theory of cross-correlation analysis of PIV images. *Appl Sci Res* 49, 191-215 (1992).

24. Westerweel, J. Fundamentals of digital particle image velocimetry. *Measurement Science and Technology* 8, 1379-1392 (1997).

25. Simerly, C., Nowak, G., de Lanerolle, P. & Schatten, G. Differential expression and functions of cortical myosin IIA and IIB isotypes during meiotic maturation, fertilization, and mitosis in mouse oocytes and embryos. *Mol Biol Cell* 9, 2509-2525 (1998).

26. Schuh, M. & Ellenberg, J. A new model for asymmetric spindle positioning in mouse oocytes. *Curr Biol* 18, 1986-1992 (2008).

27. Tinevez, J. Y. et al. Role of cortical tension in bleb growth. *Proc Natl Acad Sci USA* 106, 18581-18586 (2009).

28. Deng, M., Williams, C. J. & Schultz, R. M. Role of MAP kinase and myosin light chain kinase in chromosome-induced development of mouse egg polarity. *Dev Biol* 278, 358-366 (2005).

29. Swann, K. & Ozil, J. P. Dynamics of the calcium signal that triggers mammalian egg activation. *Int Rev Cytol* 152, 183-222 (1994).

30. Kline, D. & Kline, J. T. Repetitive calcium transients and the role of calcium in exocytosis and cell cycle activation in the mouse egg. *Dev Biol* 149, 80-89 (1992).

31. Furuta, A. et al. Microtubule disruption with BAPTA and dimethyl BAPTA by a calcium chelation-independent mechanism in 3T3-L1 adipocytes. *Endocr J* 56, 235-243 (2009).

32. Xu, N., Luo, K. Q. & Chang, D. C. Ca2+ signal blockers can inhibit M/A transition in mammalian cells by interfering with the spindle checkpoint. *Biochem Biophys Res Commun* 306, 737-745 (2003).

33. Deng, M., Suraneni, P., Schultz, R. M. & Li, R. The Ran GTPase mediates chromatin signaling to control cortical polarity during polar body extrusion in mouse oocytes. *Dev Cell* 12, 301-308 (2007).

34. Halet, G., Tunwell, R., Parkinson, S. J. & Carroll, J. Conventional PKCs regulate the temporal pattern of Ca2+ oscillations at fertilization in mouse eggs. *J Cell Biol* 164, 1033-1044 (2004).

35. Markoulaki, S., Matson, S. & Ducibella, T. Fertilization stimulates long-lasting oscillations of CaMKII activity in mouse eggs. *Dev Biol* 272, 15-25 (2004).

36. Markoulaki, S., Matson, S., Abbott, A. L. & Ducibella, T. Oscillatory CaMKII activity in mouse egg activation. *Dev Biol* 258, 464-474 (2003).

37. Shawlot, W., Deng, J. M., Fohn, L. E. & Behringer, R. R. Restricted beta-galactosidase expression of a hygromycin-lacZ gene targeted to the beta-actin locus and embryonic lethality of beta-actin mutant mice. *Transgenic Res* 7, 95-103 (1998).

38. Shmerling, D. et al. Strong and ubiquitous expression of transgenes targeted into the beta-actin locus by Cre/lox cassette replacement. *Genesis* 42, 229-235 (2005).

39. Bunnell, T. M. & Ervasti, J. M. Delayed embryonic development and impaired cell growth and survival in Actg1 null mice. *Cytoskeleton* (*Hoboken*) 67, 564-572.

40. Scott, L. Embryological strategies for overcoming recurrent assisted reproductive technology treatment failure. *Hum Fertil* (*Camb*) 5, 206-214 (2002).

41. Bromer, J. G. & Seli, E. Assessment of embryo viability in assisted reproductive technology: shortcomings of current approaches and the emerging role of metabolomics. *Curr Opin Obstet Gynecol* 20, 234-241 (2008).

42. Scott, L. The biological basis of non-invasive strategies for selection of human oocytes and embryos. *Hum Reprod Update* 9, 237-249 (2003).

43. Wong, C. C. et al. Non-invasive imaging of human embryos before embryonic genome activation predicts development to the blastocyst stage. *Nat Biotechnol* 28, 1115-1121.

44. Plusa, B. et al. Downregulation of Par3 and aPKC function directs cells towards the ICM in the preimplantation mouse embryo. *J Cell Sci* 118, 505-515 (2005).

45. Fraser, L. Ca2+ is required for mouse sperm capacitation and fertilization in vitro. *J Androl* 3, 412-419 (1982).

46. Kamm, K. E. & Stull, J. T. Dedicated myosin light chain kinases with diverse cellular functions. *J Biol Chem* 276, 4527-4530 (2001).

47. Sveen, J. An introduction to MatPIV v.1.6.1. *Mechanics and Applied Mathematics* 27 (2004).

48. Westerweel, J. Theoretical analysis of the measurement precision in particle image velocimetry. *Exp Fluids* 29, S3-S12 (2000).

49. Kimura, Y. & Yanagimachi, R. Intracytoplasmic sperm injection in the mouse. *Biol Reprod* 52, 709-720 (1995).

50. Meilhac, S. M. et al. Active cell movements coupled to positional induction are involved in lineage segregation in the mouse blastocyst. *Dev Biol* 331, 210-221 (2009).

51. Lawless, J. Negative binomial and mixed Poisson regression. *Canadian Journal of Statistics* 15, 209-225 (1987).

52. Saunders C M, Larman M G, Parrington J, Cox L J, Royse J, Blayney L M, Swann K, Lai F A. PLCζ: a sperm-specific trigger of Ca2+ oscillations in eggs and embryo development. Development 2002; 129:3533-3544.

53. Swann K, Saunders C M, Rogers N, Lai F A. PLCζ (zeta): A sperm protein that triggers Ca2+ oscillations and egg activation in mammals. Sem Cell & Dev. Biol. 2006; 17:264-73.

54. Yu Y, Saunders C M, Lai F A, Swann K. Preimplantation development of mouse oocytes activated by different levels of human phospholipase Czeta. Hum Reprod 2008; 23:365-373.

55. Rogers N T, Hobson E, Pickering S., Lai F A, Braude P, Swann K. PLCζ causes Ca2+ oscillations and parthenogenetic activation of human oocytes. Reproduction 2004; 128:697-702.

56. Yoneda A, Kashima M, Yoshida S, Terada K, Nakagwa S, Sakamoto A, Hayakawa K, Suzuki K, Ueda J, Watanabe, T. Molecular cloning, testicular expression and oocyte activation potential of porcine phospholipase C zeta. Reproduction 2006; 132:393-401.

57. Ross P J, Beyhan Z, Iager A E, Yoon S Y, Schellander K, Fissore R A, Cibelli J B. Parthenogenetic activation of bovine oocytes using bovine and murine phospholipase C zeta. BMC Dev Biol 2008; 8:16.

58. Ajduk A, Ilozue T, Windsor S, Yu Y, Seres K B, Bomphrey R J, Tom B D, Swann K, Thomas A, Graham C, Zernicka-Goetz M. Rhythmic actomyosin-driven contractions induced by sperm entry predict mammalian embryo viability. Nature Commun 2011; 2:417.

59. Summers M C, Bhatnagar P R, Lawitts J A, Biggers J D. Fertilization in vitro of mouse ova from inbred and outbred strains: complete preimplantation embryo development in glucose-supplemented KSOM. Biol Reprod 1995; 53:431-7.

60. Nomikos M, Blayney L M, Larman M G, Campbell K, Rossbach A, Saunders C M, Swann K, Lai F A. Role of Phospholipase C-ζ Domains in Ca2+-dependent Phosphatidylinositol 4, 5-Bisphosphate Hydrolysis and Cytoplasmic Ca2+ Oscillations. J Biol. Chem. 2011:280: 31011-31018.

61. Nomikos M, Elgmati K, Theodoridou M, Calver B L, Cumbes B, Nounesis G, Swann K, Lai F A. Male infertility-linked point mutation disrupts the Ca2+ oscillation-inducing and PIP(2) hydrolysis activity of sperm PLCzeta. Biochem J 2011; 434:211-217.

62. Nomikos M, Elgmati K, Theodoridou M, Calver B L, Nounesis G, Swann K, Lai F A. Phospholipase C binding to PtdIns(4,5)P2 requires the XY-linker region. J Cell Sci 2011; 124:2582-90.

The invention claimed is:

1. A method of assisted reproduction, comprising:

non-invasively capturing images of single cell mammalian embryos at a stage of development between fertilization and regression of the fertilization cone to obtain captured images;

measuring values of at least one cytoplasmic movement parameter of the single cell mammalian embryos using the captured images, the at least one cytoplasmic movement parameter comprising basal cytoplasmic speed, speed peak interval, or both;

calculating a population average of the values of the at least one cytoplasmic movement parameter based on the measuring;

assigning a grade to each single cell mammalian embryo based on the value measured relative to the calculated average, the greater the value measured, the higher the grade assigned, and an average grade assigned to the calculated population average; and selecting at least one single cell mammalian embryo having an above average grade for use in assisted reproduction; and implanting said selected single cell mammalian embryo into a female recipient;

wherein said single cell mammalian embryos are human or mouse embryos.

2. The method according to claim 1, wherein the at least one cytoplasmic movement parameter is basal cytoplasmic speed.

3. The method according to claim 2, wherein the at least one cytoplasmic movement parameter is speed peak interval, and the measuring is performed over a period of time that is sufficient to identify two successive speed peaks.

4. The method according to claim 2, wherein the basal cytoplasmic speed is measured in between speed peaks.

5. The method according to claim 1, wherein the at least one single cell mammalian embryo is at a stage of development wherein the fertilization cone is fully formed.

6. The method according to claim 5, wherein the measuring is performed throughout the period when the fertilization cone is present.

7. The method according to claim 1, wherein the at least one single cell mammalian embryo has been fertilized in vitro.

8. The method according to claim 1, wherein capturing comprises time lapse image capture followed by quantitative image analysis.

9. The method according to claim 8, wherein the images are captured from a single plane through the at least one single cell mammalian embryo.

10. The method of claim 8 wherein images are collected from a plane through the centre of the at least one single cell mammalian embryo.

11. The method according to claim 8, wherein images are collected from a plane that bisects the fertilization cone of the at least one single cell mammalian embryo.

12. The method according to claim 8, wherein the at least one single cell mammalian embryo is imaged whilst being held in a small drop of medium.

13. The method according to claim 8, wherein the image capture is completed within 4 hours of fertilization.

14. The method according to claim 8, wherein the quantitative image analysis uses particle image velocimetry (PIV).

15. The method according to claim 1, further comprising determining the probability that the at least one single cell mammalian embryo will develop to full term after transfer to a maternal recipient.

16. The method according to claim 1, wherein the at least one single cell mammalian embryo is further cultured before implantation.

17. The method according to claim 1, wherein the at least one single cell mammalian embryo is a mouse single cell embryo.

18. The method according to claim 1, wherein the at least one single cell mammalian embryo is a human single cell embryo.

19. The method according to claim 1, wherein the at least one single cell mammalian embryo selected has a calculated interval or average interval between speed peaks that is at least half a standard deviation longer than the population average interval between speed peaks, and/or having a basal cytoplasmic speed or average basal cytoplasmic speed that is at least half a standard deviation faster than the population average basal cytoplasmic speed of the population.

20. The method according to claim 1, wherein the at least one single cell mammalian embryo selected has an interval or an average interval between speed peaks that is at least one standard deviation longer than the population average interval between speed peaks, and/or having a basal cytoplasmic speed or average basal cytoplasmic speed that is at least one standard deviation faster than the population average basal cytoplasmic speed.

21. The method of claim 1, wherein the capturing comprises capturing differential interference contrast (DIC) images.

22. The method of claim 1, wherein the population average is a population mean average.

23. The method of claim 1, wherein the population average is a population median average.

24. The method of claim 1, wherein the calculating comprises calculating individual averages of the at least one cytoplasmic movement parameter and the population average is based on the individual averages.

* * * * *